US011911455B2

(12) United States Patent
Zhang et al.

(10) Patent No.: US 11,911,455 B2
(45) Date of Patent: Feb. 27, 2024

(54) HPV THERAPEUTIC NUCLEIC ACID VACCINE

(71) Applicant: Beijing Aeonvital Biomedicine Research Co., Ltd., Beijing (CN)

(72) Inventors: Xiujun Zhang, Beijing (CN); Lei Liu, Beijing (CN); Jianming Tang, Beijing (CN)

(73) Assignee: Beijing Aeonvital Biomedicine Research Co., Ltd., Beijing (CN)

( * ) Notice: Subject to any disclaimer, the term of this patent is extended or adjusted under 35 U.S.C. 154(b) by 0 days.

(21) Appl. No.: 18/237,913

(22) Filed: Aug. 25, 2023

(65) Prior Publication Data

US 2024/0009294 A1 Jan. 11, 2024

Related U.S. Application Data

(63) Continuation of application No. PCT/CN2022/134851, filed on Nov. 29, 2022.

(30) Foreign Application Priority Data

Jan. 27, 2022 (CN) .......................... 202210097009.3

(51) Int. Cl.
| | | |
|---|---|---|
| *A61K 39/12* | (2006.01) | |
| *A61P 31/20* | (2006.01) | |
| *C12N 9/22* | (2006.01) | |
| *C12N 15/11* | (2006.01) | |
| *C12N 15/70* | (2006.01) | |
| *C12N 15/90* | (2006.01) | |
| *A61K 39/00* | (2006.01) | |

(52) U.S. Cl.
CPC .............. *A61K 39/12* (2013.01); *A61P 31/20* (2018.01); *C12N 9/22* (2013.01); *C12N 15/111* (2013.01); *C12N 15/70* (2013.01); *C12N 15/902* (2013.01); *A61K 2039/53* (2013.01); *A61K 2039/55516* (2013.01); *C12N 2310/20* (2017.05); *C12N 2710/20034* (2013.01)

(58) Field of Classification Search
None
See application file for complete search history.

(56) References Cited

U.S. PATENT DOCUMENTS

| | | | | |
|---|---|---|---|---|
| 5,955,087 A | * | 9/1999 | Whittle | .................. A61P 37/04 |
| | | | | 435/235.1 |
| 10,071,150 B2 | * | 9/2018 | Bian | ..................... C07K 14/535 |
| 2011/0287039 A1 | | 11/2011 | Frazer et al. | |
| 2019/0134181 A1 | * | 5/2019 | Dutton | ................... C12N 15/85 |

FOREIGN PATENT DOCUMENTS

| | | |
|---|---|---|
| CN | 101591646 A | 12/2009 |
| CN | 103864936 A | 6/2014 |
| CN | 108424925 A | 8/2018 |
| WO | 2016191545 A1 | 12/2016 |

OTHER PUBLICATIONS

Notice of Allowance of counterpart Chinese Patent Application No. 202210097009.3 dated Apr. 2, 2022.
First Office Action of counterpart Chinese Patent Application No. 202210097009.3 dated Mar. 11, 2022.
Janin Chandra et al., DNA Vaccine Encoding HPV16 Oncogenes E6 and E7 Induces Potent Cell-mediated and Humoral Immunity Which Protects in Tumor Challenge and Drives E7-expressing Skin Graft Rejection, J Immunother, Mar. 31, 2017, pp. 62-70, vol. 40, No. 2.
Juan Liu et al., Linkage of Modified HPV16 E7 Gene to HSP70 Can Enhance the Potency of DNA Vaccine, Journal of Xianning College (Medical Sciences), Oct. 30, 2003, pp. 305-309, vol. 17, No. 5.
Chu Xiao-Jie et al., Development of a HPV16 E7 CTLs Peptides-based Virus-like Particle Therapeutic Vaccine, China Biotechnology, Feb. 15, 2015, pp. 45-51, vol. 35, No. 2.
Ma Zheng-Hai et al., Polymorphism of HPV-16 type L2 genes from cervical carcinoma biopsies in southern Xinjiang Uygur women, Chin J Microbiol Immunol, Dec. 30, 2004, pp. 968-972, vol. 24, No. 12.

* cited by examiner

*Primary Examiner* — Shanon A. Foley

(57) ABSTRACT

The nucleic acid sequences provided by the present invention comprises sequence HPV16-AVLS1 and sequence HPV16-AVLC1 in a 1:1 ratio; and sequence HPV18-AVLS1 and sequence HPV18-AVLC1 in a 1:1 ratio; the sequence AVLS1 and the sequence AVLC1 comprise two concatenated E6 proteins, two LI short peptides, two L2 short peptides, two concatenated E7 proteins, one PADRE sequence, and one adjuvant sequence respectively; the N-terminal of sequence AVLS1 carries a mouse IgK secretion peptide sequence; the N-terminal of sequence AVLC1 carries a ubiquitin sequence. The nucleic acid sequences provided by the present invention can not only induce high titer antibodies against E6/E7, but also elicit a high level of functional cellular immune, demonstrating excellent preventive and therapeutic effects against tumors related to HPV.

17 Claims, 13 Drawing Sheets

Specification includes a Sequence Listing.

HPV THERAPEUTIC NUCLEIC ACID VACCINE

CROSS-REFERENCE TO RELATED APPLICATIONS

The present application is a continuation application of PCT application No. PCT/CN2022/134851 filed on Nov. 29, 2022, which claims the benefit of Chinese Patent Application No. 202210097009.3 filed on Jan. 27, 2022. The contents of all of the aforementioned applications are incorporated by reference herein in their entirety.

Reference to Sequence Listing

The Sequence Listing XML file submitted via the USPTO Patent Center, with a file name of "Sequence_listing_TREENIE-23013-USPT.XML", a creation date of Aug. 21, 2023, and a size of 42 KB, is part of the specification and is incorporated in its entirety by reference herein.

TECHNICAL FIELD

The present invention relates to tumor immunotherapy and prevention, specifically to HPV therapeutic Nucleic Acid vaccine.

BACKGROUND

Approximately 20-25% of cancer cases worldwide are caused by infectious sources, with about 15% of human cancers associated with viral infections. Human papillomavirus (HPV) is responsible for approximately 30% of all infectious source-related cancers and over 95% of cervical cancers. In 2018, more than 300,000 women worldwide died from cervical cancer, which is a result of persistent high-risk HPV (hrHPV) infection.

Currently, preventive HPV vaccines are available on the market, which induce type-specific neutralizing antibodies against the major capsid protein L1 to prevent persistent cervical infections.

However, these vaccines have limited effectiveness in treating pre-existing HPV infections or precancerous lesions. Additionally, existing treatment methods for cervical cancer are limited in efficacy, and the HPV vaccination rates are suboptimal worldwide. HPV infection and subsequent HPV-related malignancies will remain a public health issue for decades to come. Therefore, the development of therapeutic HPV vaccines and other cancer therapies is an urgent task.

The early proteins E6 and E7 are known to be responsible for the malignant progression of HPV-related cancers. E6 can bind to and degrade the tumor suppressor factor p53, while E7 inhibits pRb, leading to uncontrolled cell cycle progression into the S phase. Thus, HPV E6 and E7 oncoproteins are ideal targets for therapeutic HPV vaccines, and the majority of HPV therapeutic vaccines currently target these two antigens. However, these vaccines targeting E6 and E7 have limited effectiveness against HPV-related cancers. The main reasons may include: moderate expression of E6 and E7 in epithelial basal membrane cells, successful evasion of the immune response against highly overexpressed E6 and E7 before it is upregulated in malignant cells, resulting in persistent virus infections; limited antigenic epitopes due to the small size of E6 and E7 proteins; low expression efficiency, low delivery efficiency, and imperfect structural design of existing therapeutic vaccine antigens, resulting in insufficient immune response intensity. Therefore, a broader antigen targeting strategy and antigen sequence design may be needed to treat HPV+ cancers and clear persistent precancerous infections.

HPV has two capsid proteins, L1 and L2, with L1 being the major capsid protein and L2 stabilizing the virus capsid structure. The current HPV preventive vaccines assemble into virus-like particles (VLPs) after expression of L1 protein, which can induce neutralizing antibodies in human body and perform good efficacy in preventing HPV infections. VLPs as subunit protein vaccines stimulate weak cellular immune responses, resulting in limited therapeutic effects. Studies have shown that DNA vaccine forms of both L1 and L2 can induce strong humoral and cellular immune responses simultaneously, highlighting their potential as therapeutic vaccine targets.

SUMMARY OF INVENTION

The present invention designs a novel HPV therapeutic nucleic acid vaccine AVL101 nucleic acid sequence, through: antigen sequence design and codon optimization of E6, E7, L1, and L2 of HPV16 and HPV18; fusion of L1/L2 helper T cell epitope, two full-length E6 and two full-length E7 proteins, adjuvant sequence Beta defensin-3, and universal Th epitope PADRE sequence. The AVL101 includes four nucleic acid sequences, each vaccine sequence not only containing two full-length E6 proteins and two full-length E7 proteins, but also containing the immune epitope sequences of L1/L2 helper T cells. The sequence combination can not only induce high titer antibodies against E6/E7, but also effectively stimulate T cell immunity, ultimately exhibiting the efficacy in inhibiting the growth of E6/E7-expressing cancer cells.

Specifically, the invention provides a nucleic acid sequence for the treatment and prevention of HPV infection diseases, comprising:

sequence HPV16-AVLS1 and sequence HPV16-AVLC1 in a 1:1 ratio;

and, sequence HPV18-AVLS1 and sequence HPV18-AVLC1 in a 1:1 ratio;

preferably, HPV16-AVLS1, HPV16-AVLC1, HPV18-AVLS1 and HPV1 8-AVLC1 in a 1:1:1:1 ratio;

wherein, the sequence AVLS1 and the sequence AVLC1 include two concatenated protein E6 molecules, two L1 short peptides, two L2 short peptides, two concatenated protein E7 molecules, one PADRE sequence, and one adjuvant sequence respectively.

The L1 short peptide is selected from at least one of the sequences shown in SEQ ID No: 1 to SEQ ID No: 4;

the L2 short peptide is selected from at least one of the sequences shown in SEQ ID No: 5 to SEQ ID No: 8;

the N-terminal of sequence AVLS1 carries a mouse IgK secretion peptide sequence; the N-terminal of sequence AVLC1 carries a ubiquitin molecule.

The present invention provides DNA vaccine sequences for treating diseases related to HPV16 or HPV18 infections, or coinfection of both, through antigen sequence combination design and codon optimization of E6, E7, L1, and L2 of HPV16.

The AVLS1 and AVLC1 codon protein sequences of the present invention differ only at the N-terminus, while the remaining sequences are the same. The N-terminus of AVLS2 carries a mouse IgK secretion peptide sequence, which promotes protein secretion to the outside of the cell for capture and presenting by antigen-presenting cells, thus enhancing helper T cell immune responses; on the other hand, AVLC1 contains one ubiquitin molecule, which facilitates protein degradation and enhances CD8+ T cell immunity. The remaining common parts include two full-length E6 molecules, two L1 short peptides, two L2 short peptides, two full-length E7 molecules, one PADRE sequence, and one adjuvant sequence. The short peptides of L1 and L2 provided by the invention are helper T cell epitopes, which, when introduced into the DNA vaccine sequence, can help stimulate and enhance CTL (cytotoxic T lymphocyte) killing of HPV-infected cells.

To overcome the high polymorphism of HLA-2 alleles, the present invention incorporates a universal PADRE (Pan-HLA DR) sequence during the construction process; wherein, the PADRE sequence is SEQ ID No: 9.

Additionally, in the present invention, one adjuvant peptide beta-defensin-3 is added at the C-terminus, which acts as a Toll-like receptor agonist to promote innate immunity. Wherein, the adjuvant sequence is SEQ ID No: 10.

Wherein, the mouse IgK secretion peptide sequence is SEQ ID No: 11;

Wherein, the ubiquitin molecule sequence is SEQ ID No: 12.

Wherein, AGA (Ala-Gly-Ala) or AAY (Ala-Ala-Tyr) linkers are used between the various components, while a rigid linker EAAAK (Glu-Ala-Ala-Ala-Lys) (SEQ ID NO:19) is used for the link of adjuvant peptide. These linkers will ensure maximum immunogenicity and epitope presentation. The final vaccine structure is shown in FIG. 1.

The HPV16 fusion protein E6 sequence provided by the present invention introduces C70G and 1135T mutations, while the HPV18 fusion protein E6 sequence introduces C65G and 1130T mutations, eliminating their ability to degrade p53;

the HPV16 E7 protein sequence introduces C24G and E26G mutations, while the HPV18E7 protein sequence introduces C27G and E29G mutations, rendering them incapable of malignant transformation.

Preferably, the nucleic acid sequence is one of the four sequences as shown in SEQ ID No: 13 to SEQ ID No: 16.

The present invention uses HPV16 and 18 subtypes as examples, which can induce specific humoral immune and cellular immune responses against E6 and E7. The HPV16 vaccine sequence demonstrates efficient inhibition of TC-1 tumor growth expressing HPV16E6/E7. By comparing vaccine sequences designed by the present invention with HPV DNA vaccine sequence of VGX3100, the fastest progressing in clinical currently and already in phase III clinical trials, the vaccine of sequences of the present invention exhibit better immune response efficacies and anti-tumor effects. The sequence design method of the present invention can also be applied to the development of therapeutic vaccines for other HPV subtype-related diseases.

The vaccine DNA sequences provided by the present invention can exist independently, be linked to eukaryotic expression vectors, or be converted into mRNA sequences, as vaccine components.

In other words, the mRNA sequences derived from the nucleic acid sequences provided by the present invention can be used as vaccine components.

Another objective of the present invention is to provide a recombinant vector comprising an expression vector and any of the aforementioned nucleic acid sequences.

Wherein, the ends of the sequence AVLS1 and sequence AVLC1 are ligated into the expression vector AVL0318 using HindIII and XhoI restriction enzyme sites. The expression vector is an antibiotic-free AVL0318 vector.

Another objective of the present invention is to provide a preparation method for amplifying the above recombinant vector, comprising the following steps:

1) synthesizing four nucleic acid sequences of the vaccine sequences HPV16-AVLS1, HPV16-AVLC1, HPV18-AVLS1 and HPV18-AVLC1 by splicing the amino acid sequences of E6/E7 proteins, L1/L2 peptides, IgK, ubiquitin, PADRE, and adjuvant; preferably synthesize as shown in SEQ ID No: 13 to SEQ ID No: 16;

2) inserting the above four nucleic acid sequences into the PUC57 vector using HindIII and XhoI restriction enzyme sites, and then subcloning the vaccine sequences into the expression vector AVL0318; obtaining four recombinant vectors AVL0318-HPV16/18-AVLS1/AVLC1;

3) amplifying the plasmids of AVL0318-HPV16/18-AVLS1/AVLC1 using *Escherichia coli* AVL-DH5α (SacB).

Wherein, the genome sequence of *Escherichia coli* AVL-DH5α(SacB) contains the SacB gene for constitutive expression and does not contain antibiotic selection markers;

wherein, the sequence capable of expressing the SacB gene is shown as SEQ ID No: 17.

The preparation method of the *Escherichia coli* strain AVL-DH5α(SacB) provided by the present invention: the SacB gene is inserted into the attB site of the *Escherichia coli*; the gene editing is achieved by a method comprising the following steps:

1) PCR amplification of the upstream and downstream homologous arm gene sequences of the insertion site, p5/6 6/6-SacB gene sequence respectively, and overlapping extension PCR with the three sequences as templates to amplify the long fragment SacB-CRISPR nucleotide sequence; the nucleotide sequence of SacB-CRISPR is shown as SEQ ID No: 18;

2) Transforming the Cas9 expression plasmid, sgRNA, and the long fragment SacB-CRISPR nucleotide sequence into *Escherichia coli* DH5α competent cells, performing gene editing and homologous recombination repair, selecting single clones for culture, and verifying by PCR sequencing; finally, eliminating the resistance of tool plasmid and the edited strain by the temperature-sensitivity to obtain the AVL-DH5α (SacB) strain suitable for target plasmid without antibiotics selection.

The present invention further provides a method for producing antibiotic-free screening marker plasmids by strains, comprising the following steps:

1) AVL-DH5 α(SacB) strain is coated on LB (Luria-Bertani) culture medium with 6% sucrose and cultured at 37° C. for 24 h. The above strains can not grow.

2) Prepare AVL-DH5 α(SacB) receptive cells, transformed into AVL0318 plasmids containing RNA-out gene fragments that inhibit SacB expression. The above strains can grow when they are coated on LB culture medium with 6% sucrose and cultured at 37° C. for 24h.

The invention transfers SacB gene (sucrose lethal allele) into *Escherichia coli* by CRISPR-cas9 technology; SacB encodes sucrose polysaccharide enzyme, which can catalyze the hydrolysis of sucrose into glucose and fructose, and polymerize fructose into high molecular weight fructan, whose accumulation is toxic to cells and can cause the death of *Escherichia coli*. The plasmid system constructed by the present invention contains target fragments of HPV and RNA-out gene fragments that inhibit the expression of SacB. When the plasmid system is introduced into recombinant *Escherichia coli*, a sequence will be expressed by the RNA-out genes on the plasmid, silencing the SacB gene.

Even if cultured in a medium with sucrose, the *Escherichia coli* still does not die. This can quickly distinguish strains that have been transferred with the HPV vaccine recombinant vector from strains that have not been transferred with the recombinant vector.

The novel HPV therapeutic nucleic acid vaccine provided by the present invention, comprises any of the aforementioned nucleic acid sequences, or a mRNA sequence transformed from the nucleic acid sequences, or a recombinant vector comprising the nucleic acid sequences, as well as a recombinant vector prepared by the aforementioned preparation method.

The present invention provides a novel system solution suitable for the development and application of HPV therapeutic nucleic acid vaccines of different subtypes by combining the design method of an HPV therapeutic vaccine, an efficient and safe expression vector, and a high yield and safe plasmid production strain.

The DNA vaccine sequence composition provided by the present invention can not only induce high titer antibodies against E6/E7, but also effectively stimulate T cell immunity, ultimately effectively inhibiting the growth of cancer cells expressing E6/E7. The DNA vaccine sequence design method can be simultaneously applied to various subtypes of HPV, such as high-risk HPV16, 18, 58, 52, 33. These five subtypes account for about 90% of precancerous lesions and cervical cancer in all populations worldwide. Therefore, the present invention can be used to treat infectious diseases of different subtypes of HPV.

DETAILED DESCRIPTION

The following examples are used to illustrate the present invention, but are not intended to limit its scope.

A nucleic acid sequence AVL101 for treating HPV infection diseases of the present invention, includes two nucleic acid sequences of HPV16 and two nucleic acid sequences of HPV18; which are respectively HPV16-AVLS1 and HPV16-AVLC1; HPV18-AVLS1 and HPV18-AVLC1.

The AVLS1 and AVLC1 codon protein sequences of the HPV16 and 18 differ only at the N-terminus, while the remaining sequences are the same. The N-terminus of AVLS1 carries a mouse IgK secretion peptide sequence, which promotes protein secretion to the outside of the cell for capture and presenting by antigen-presenting cells, thus enhancing helper T cell immune responses; on the other hand, AVLC1 contains one ubiquitin molecule, which facilitates protein degradation and enhances CD8+ T cell immunity.

Figure 1:
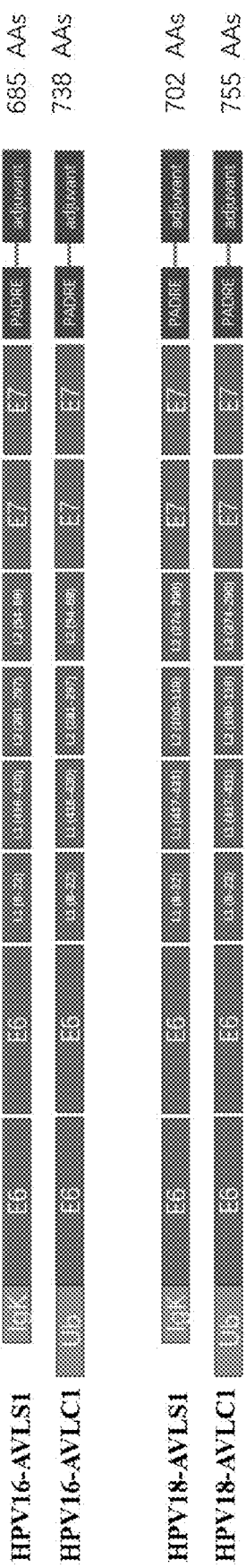
FIG. 1 is a schematic diagram of the structure of the HPV therapeutic nucleic acid vaccine provided by the present invention.

The remaining common parts include two concatenated full-length E6 molecules, two L1 short peptides, two L2 short peptides, two concatenated full-length E7 molecules, one PADRE sequence, and one adjuvant sequence. The short peptides of L1 and L2 are helper T cell epitopes, the reason why they are introduced into our DNA vaccine sequence is that they can help stimulate and enhance CTL killing of HPV-infected cells; to overcome the high polymorphism of HLA-2 alleles, a universal PADRE (Pan-HLA DR) sequence is incorporated during the construction process; meanwhile, one adjuvant peptide beta-defensin-3 is added at the C-terminus, which acts as a Toll-like receptor agonist to promote innate immunity. AGA (Ala-Gly-Ala) or AAY (Ala-Ala-Tyr) linkers are used between the various components; a rigid linker EAAAK (Glu-Ala-Ala-Ala-Lys) (SEQ ID NO:19) is used for adjuvant peptide. These linkers will ensure maximum immunogenicity and epitope presentation. The final vaccine structure is shown in FIG. 1.

Besides, the HPV16 fusion protein E6 sequence introduces C70G and I135T mutations, while the HPV18 fusion protein E6 sequence introduces C65G and I130T mutations, eliminating their ability to degrade p53; the HPV16 E7 protein sequence introduces C24G and E26G mutations, while the HPV18 E7 protein sequence introduces C27G and E29G mutations, rendering them incapable of malignant transformation.

The present invention designs a novel HPV therapeutic nucleic acid vaccine through: fusion of L1/L2 helper T cell epitope, two full-length E6/E7 proteins, adjuvant sequence Betadefensin-3 and universal Th epitope PADRE sequence. The present invention uses two subtypes of HPV16 and 18 as examples, which can induce specific humoral immune and cellular immune responses against E6 and E7 and the HPV vaccine sequence demonstrates efficient prevention and inhibition effects on TC-1 tumor cell. By comparing vaccine designed by the present invention with HPV DNA vaccine sequence of the fastest progressing in clinical currently and already in phase III clinical trials, the corresponding vaccines of the sequences of the present invention exhibit better immune response efficacies and anti-tumor effects. The sequence design method of the present invention can also be applied to the development of therapeutic vaccines for other HPV subtype-related diseases.

The present invention also provides expression vectors and plasmid production strains for use as DNA vaccines. The commonly used expression vectors currently use antibiotic resistance such as KanR and AmpR as selection markers. Adding corresponding antibiotics to the fermentation medium to maintain selection pressure can stabilize the presence of plasmids in the cell. Antibiotics, as traditional selective markers, have a wide range of applicability and effectiveness at the laboratory research and industrial production levels, making them one of the most convenient tools. However, the overuse of antibiotics in healthcare has become a serious problem. Many pathogenic bacteria have mutated and developed related resistance under the widespread use of antibiotics, and related antibiotics are no longer able to control their growth and infection. In addition, resistance genes are usually located on movable plasmid DNA units, which can be transmitted between different hosts, ultimately leading to the transfer of resistance genes to other microorganisms in the environment. Regulatory agencies such as the US Food and Drug Administration (FDA) and the World Health Organization (WHO) believe that the presence of antibiotic resistance genes in plasmid skeletons is not welcome and the use of antibiotic resistance genes in final commercial products such as DNA vaccines needs to be avoided. They believe that in addition to the possibility of antibiotic resistance transferring to endogenous microbiota, plasmid resistance genes also have a certain probability of integrating into human chromosomes, activating and transcribing related oncogenes. For example, regulatory guidelines on DNA vaccine plasmids state that "the use of certain selective markers such as antibiotic resistance should be avoided, which may have adverse effects on other clinical treatments in the target population. In addition, the use of antibiotics in fermentation culture requires expensive process validation for antibiotic removal during plasmid purification. Therefore, considering the above factors, the present invention adopts a plasmid screening strategy without antibiotics.

The present invention is based on commonly used *Escherichia coli* strains and utilizes CRISPR/Cas9 technology to knock in *Escherichia coli* DH5 α optimized SacB gene sequence to prepare the strain AVL-DH5a (SacB), making it suitable for antibiotic-free plasmid production. The present invention utilizes RNA based selectable marker to screen and maintain plasmids. However, unlike the *Escherichia coli* SacB expression strain invented by Luke et al. using homologous recombination, which needs Chloramphenicol resistance genes to screen the recombinants, the invention uses a more convenient CRISPR/Cas9 technology, and does not need additional resistance genes to select *Escherichia coli* recombinants, and the safety of the host strain produced with AVL-DH5 α (SacB) strain as a plasmid is higher. In addition, compared to the SacB expression strain invented by Luke, the strain of the present invention has optimized the codon of SacB, resulting in higher expression of SacB in *Escherichia coli*. The final screened recombinant strain is more sensitive to sucrose, has higher efficiency in screening non-resistant plasmids, and can significantly increase plasmid production.

The present invention provides a novel system solution suitable for the development and application of HPV therapeutic nucleic acid vaccines of different subtypes by combining the design method of HPV therapeutic nucleic acid vaccine, an efficient and safe expression vector, and a high yield and safe plasmid production strain.

EXAMPLE 1 Design Scheme, Construction and Preparation of Nucleic Acid Sequences

1. Acquisition of HPV16/18 E6, E7, L1 and L2 target fragments

The DNA and protein sequences of E6/E7 and L1/L2 of HPV16 strain NC_001526.4 were downloaded from GenBank;

The DNA and protein sequences of E6/E7 and L1/L2 of HPV18 strain AY262282.1 were downloaded from GenBank.

2. Sequence Optimization

After all sequences were spliced according to the vaccine protein structure, HPV16-AVLS1 and HPV16-AVLC1 contained 685 and 738 amino acids respectively, HPV18-AVLS1 and HPV18-AVLC1 contained 702 and 755 amino acids respectively, and then codons were optimized. These optimization methods included but were not limited to: human codon use preference, moderate GC-content, stable mRNA secondary structure, etc, eliminating duplicate sequences, hiding splicing sites, and unnecessary restriction enzyme cleavage sites, while preventing depletion of tRNA libraries in cells.

3. Sequence Synthesis and Construction of Recombinant Plasmids

The optimized sequence was gene synthesized directly, and connected to the vector PUC57 using HindIII and XhoI enzyme digestion sites. Subsequently, the vaccine sequence was cloned into the expression vector AVL0318.

Figure 2:
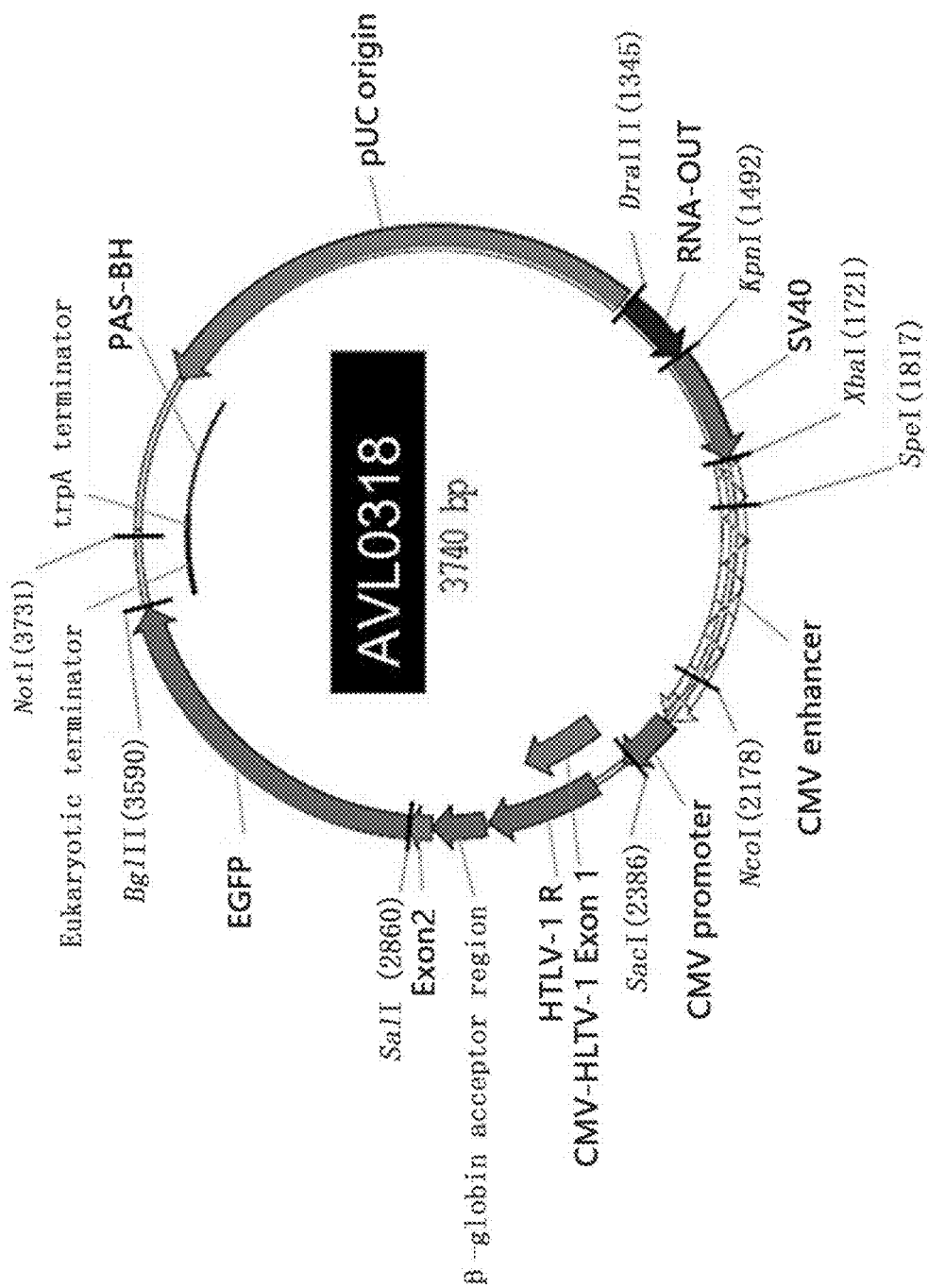
FIG. 2 shows the AVL0318 carrier spectrum.

Specifically, AVL0318 and PUC57 HPV16/18-AVLS1/AVLC1 were double enzyme digested by HindIII and XhoI, went through agarose gel electrophoresis, and the vector AVL0318 and target band HPV16/18-AVLS1/AVLC1 were purified and recovered. Afterwards, HPV16/18-AVLS1/AVLC1 was connected to the AVL0318 vector respectively through T4DNA ligase. The map of AVL0318 vector is shown in FIG. 2.

EXAMPLE 2 Enzyme Digestion and Expression Identification of Recombinant Plasmid

1. Enzyme digestion identification

The plasmids of AVL0318-HPV16/18-AVLS1/AVLC1 were amplified respectively by using *Escherichia coli* AVL-DH5a (SacB), and then purified using an endotoxin free plasmid extraction kit.

Figure 3:
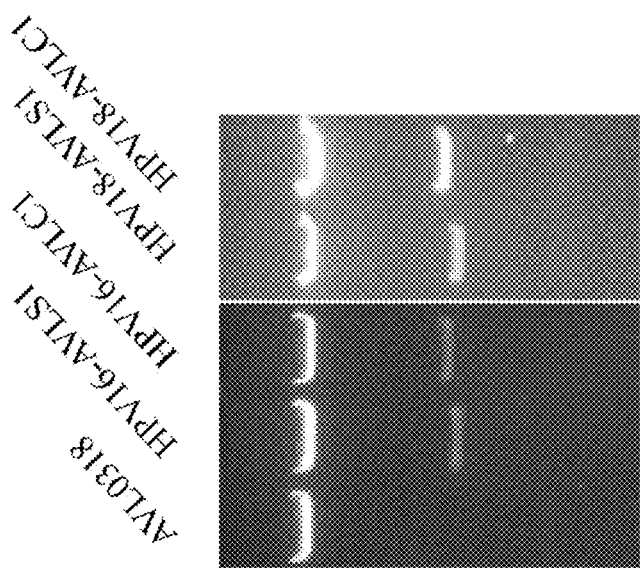
FIG. 3 shows the enzyme digestion identification diagram of the vaccine sequence expression plasmid provided by the present invention.

The specific operation method is as follows:
1) AVL-DH5 α (SacB) strain was cultured on 6% sucrose LB medium at 37° C. for 24h.
2) The plasmid extraction kit was used for plasmid extraction.
3) HindIII and XhoI double enzyme digestion was utilized to verify the correctness of the plasmid, and sequence was tested to verify the correctness of the sequence, as shown in FIG. 3.

2. Expression Identification

Figure 4:
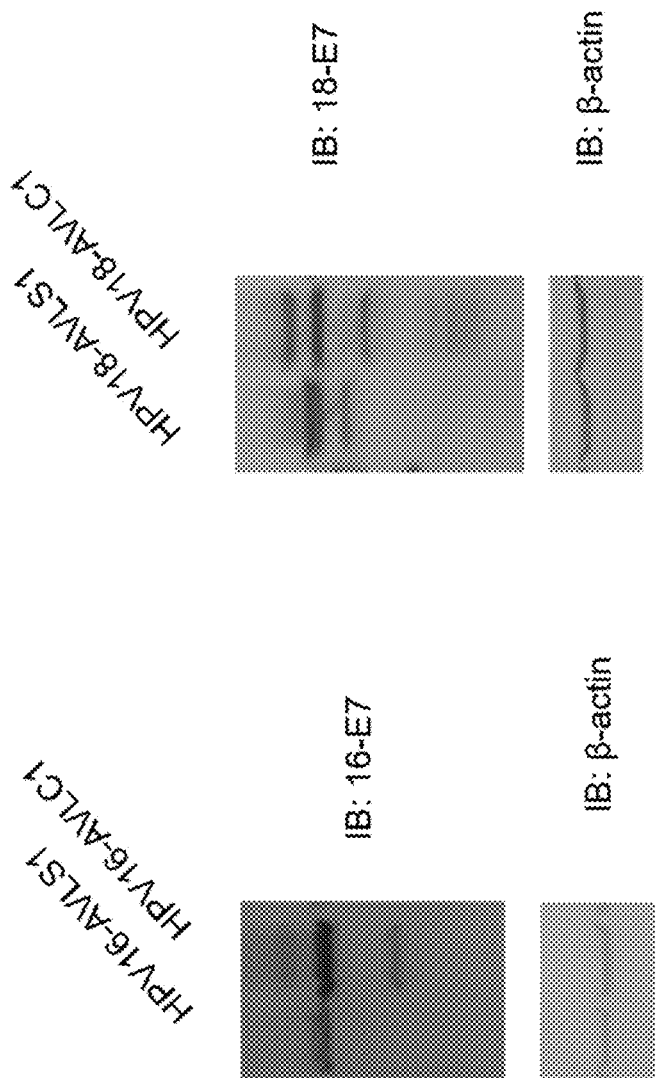
FIG. 4 shows the expression detection diagram of the vaccine sequence plasmid provided by the present invention in HEK-293T cells.

HEK-293T cell line was used for plasmid expression identification. A 6-well plate was used to culture HEK-293T cells, and lipofectamine 2000 was used to transfer 1.5m plasmid into the cells. After 48 hours of transfection, the cells were harvested for Western Blo identification. All four recombinant vectors can be effectively expressed in HEK-293 cells; as shown in FIG. 4.

Example 3 Cell Immunoassay 3.1 Immunization, C57BL/6J mice were administered subcutaneously at 2-week intervals on the auricles of each ear with 30 μg HPV16DNA vaccine AVL0318-AVLS1 and AVL0318-AVLC1 (1:1) or 30 μg HPV18 DNA vaccine AVL0318-AVLS1 and AVL0318-AVLC1 (1:1) (plasmid dissolved in TE buffer, i.e. 15 μg (20 μL)/Ear), and immunized for 3 times. 3-5 mice were used per group. The immune response was tested one week after the completion of three immunizations. The specific cellular immune response to E6 and E7 was detected by ELISPOT from mouse splenocyte.

3.2 ELISPOT Detection
3.2.1 Splenocyte Acquisition

About 500 μL blood samples were taken from mice to a 1.5 mL EP tube, left still at room temperature for about 1 hour, and the serum was taken and packaged for storage at −80° C. The mice were decapitated and killed. After soaking in alcohol for 5 minutes, the mice were transferred to a super clean table, and the spleen was taken after laparotomy. The prepared spleen was gently grinded, poured multiple times into PBS to rinse the single cells that were grinded out, centrifuged and harvested, 300 g, and centrifuged for 5 minutes.

3.2.2 Lysis of Red Blood Cells

The supernatant was discarded, 10 mL of red blood cell lysate and approximately 10 mL of PBS were added to each tube, let stand for 2-3 minutes, 300 g, centrifuged for 5 minutes, and the supernatant was discarded.

3.2.3 Cell Cleaning and Resuspension 10 mL of 1640 suspension in 5% FBS was used, cleaned once, centrifuged at the same speed, the supernatant discarded, 10 mL of 10% FBS in 1640 was add to suspense, and mixed well. 20 μL was taken for count. The cell concentration was adjusted at $2\times10^6$/mL, i.e. $2\times10^5$/100 μL.

3.2.4 Orifice Plate Cleaning and Laying (1) 96 well plate wetting: The 96 well plate was taken from the reagent kit and added PBS 200 μL/well to clean the twice, then added 1640 culture medium in 10% FBS for 200 μL/well, placed in a 37° C. incubator for 30 minutes;

(2) Cell laying: The culture medium was discarded and added 100 μL diluted cells;

(3) Antigen formulation: formulation of single peptide: the final concentration was 20 μg/mL, formulation of multiple peptides: the final concentration of each polypeptide was 2m/mL; PMA was formulated with a final concentration of 50 ng/mL;

(4) 100 μL corresponding antigens was added each well to the 96 well plate with cells laid. Control was supplemented with 100 μL medium and incubated in a 5% $CO_2$ incubator at 37° C. for 24 hours.

3.2.5 IFN-γ Secretory Cell Detection (CTL ELISPOT Kit)

(1) Cleaning: The incubated 96 well plate was taken out, the supernatant was discarded, cleaned twice with 200 μL PBS/hole, and cleaned twice with 200 μL PBST (0.05% tween20)/hole;

(2) Test antibody preparation: 10 μL detection antibody was added to 10 mL Diluent B, 80 μL per well and incubated at room temperature for 2 hours;

(3) The supernatant was abandoned and washed the plate 3 times with 200 μL PBST/hole;

(4) Secondary antibody formulation: 10 μL Strep-AP secondary antibody was added to 10 mL Diluent C, 80 μL per well and incubated at room temperature for 30 minutes;

(5) The supernatant was discarded, cleaned twice with 200 μL PBST/hole, and cleaned twice with pure water;

(6) Blue Developer solution preparation: 10 mL Diluent Blue was added with 160 μL S1 and mixed well, then added with 160 μL S2 and mixed well, and then 92 μL S3 and mixed well. The 96 well plate was added 80 μL each well and incubated at room temperature for 15-30 minutes;

(7) The supernatant was discarded, and the plate was cleaned three times with 200 μL pure water/hole;

(8) each row of holes on the 96 well plate was removed, the white film at the bottom was cleaned in pure water and no need to install them back. Each row of holes was placed on the 96 well plate rack at room temperature overnight to dry, and read the plate.

3.3 Result Analysis

Figure 5A:
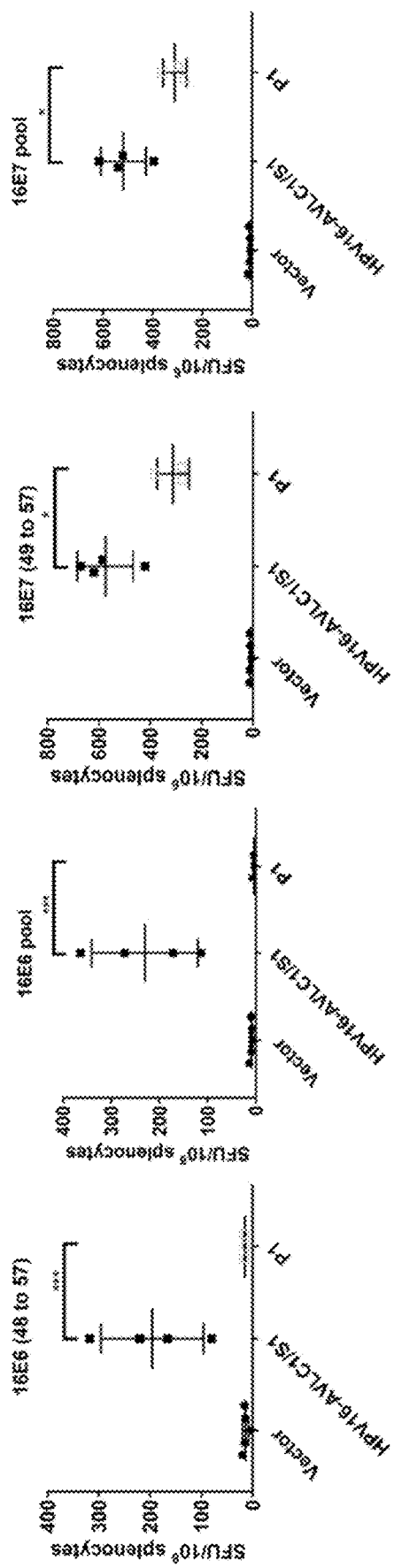
FIG. 5*a* shows the results of HPV16 E6 and E7 specific cellular immune testing.

The specific secretion of y-interferon of HPV16 DNA vaccine was shown in FIG. 5a below. Wherein, P1 and P2 are the fastest progressing cervical cancer therapeutic DNA vaccines in the world, which are currently in Phase III clinical trials respectively. P1 and P2 are the E6E7 fusion expression plasmids of HPV16 and HPV18, respectively, and were used as positive controls here. The results showed that the vaccine sequence provided by the present invention can simultaneously stimulate cellular immunity targeting E6 and E7, while the control P1 can only induce specific cellular immunity of E7. Meanwhile, the specific cellular immunity of E7 stimulated by the HPV16 DNA vaccine of the present invention are significantly higher than P1.

Figure 5B:
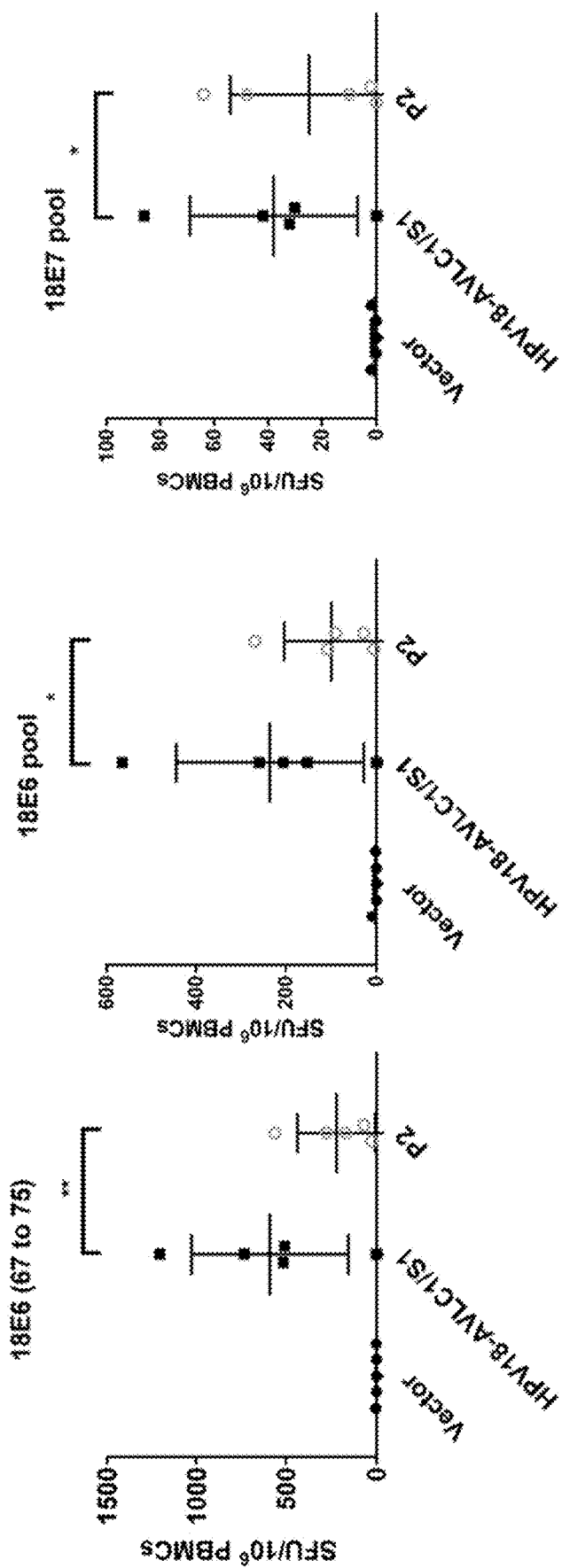
FIG. 5*b* shows the results of HPV18 E6 and E7 specific cellular immune testing.

The specific secretion of y-interferon of HPV18 DNA vaccine was shown in FIG. 5b below. The results showed that both the vaccine sequence of the present invention and P2 can simultaneously stimulate cellular immunity targeting E6 and E7, but the efficacy of the present vaccine is significantly higher than that of the control group P2.

EXAMPLE 4 ELISA Detection of Antibody Response to E6 and E7 (Humoral Immunity)

One week after the completion of the three immunizations, blood was taken from the orbit to detect E6 and E7 specific humoral immunity.

4.1 Operation Steps
4.1.1 Preparation of Antigen Coating Plate
(1) Preparing CBS buffer solution (0.05 mol/L, pH 9.6)

| Sodium carbonate | 1.59 g |
| Sodium bicarbonate | 2.93 g |

900 ml ultrapure water was added to dissolve, the pH was adjusted to 9.6, and ultrapure water was added to constant volume of 1L. The solution was stored at 4° C.

(2) Antigen Coating

The E6 and E7 protein stock of HPV16/18 was diluted to 5 μg/mL using the CBS prepared in (1). 96 well plate (Corning 3590) was coated with the diluted antigen solution (100 μL/hole), sealed and placed at 4° C. overnight in a refrigerator;

4.1.2 Sealing Antigen Coating Plate (1) Preparation of PBST washing solution (0.01 mol/L, pH 7.4, PBS, containing 0.05% Tween 20)

(2) Preparation of sealing solution (5% skim milk powder)—prepared on site the next day skim milk powder 5 g

| PBST | 100 mL |

(3) The cover plate was washed with PBST washing solution three times and sealed at room temperature for 2 hours with sealing solution (100 μL/hole);

4.1.3 Sample Preparation and Incubation (1) The serum was diluted. The serum was diluted with blocking buffer at a ratio of 1:100 per well, i.e. 198 μL diluent and 2 μL serum to be tested were added each well.

(2) The 96 well plate was covered with lid, vibrated (500 rpm) and incubated at 37° C. for 1 hour.

4.1.4 Secondary Antibody Incubation (1) The secondary antibody (HRP anti-mIgG) was diluted with blocking buffer at a ratio of 1:8000.

(2) The plate was washed 5 times with PBST washing solution after the completion of the first antibody incubation; Each hole was added 50 μL secondary antibody diluent. The 96 well plate was covered with lid, vibrated (500 rpm) and incubated at 37° C. for 1 hour 4.1.5 Color Rendering The board was washed 5 times with PBST washing solution and added with TMB chromogenic agent (50 μL/well), the lid was covered and incubated at room temperature for 5-20 minutes (depending on color development of the reaction);

4.1.6 Termination Reaction (1) Preparation of termination solution (2 M H2SO4)—acid in water

| Concentrated sulfuric acid | 11.1 mL |
|---|---|
| Ultrapure water | 89.9 mL; |

(2) According to the color development results of the reaction, a termination solution was added, 50 μL/hole, to terminate the reaction;

4.1.7 Detection

The OD450 absorbance value was detected using an enzyme-labeled instrument, and analyzed using GraphPad Prism and plotted.

4.2 Result Analysis

Figure 6A:
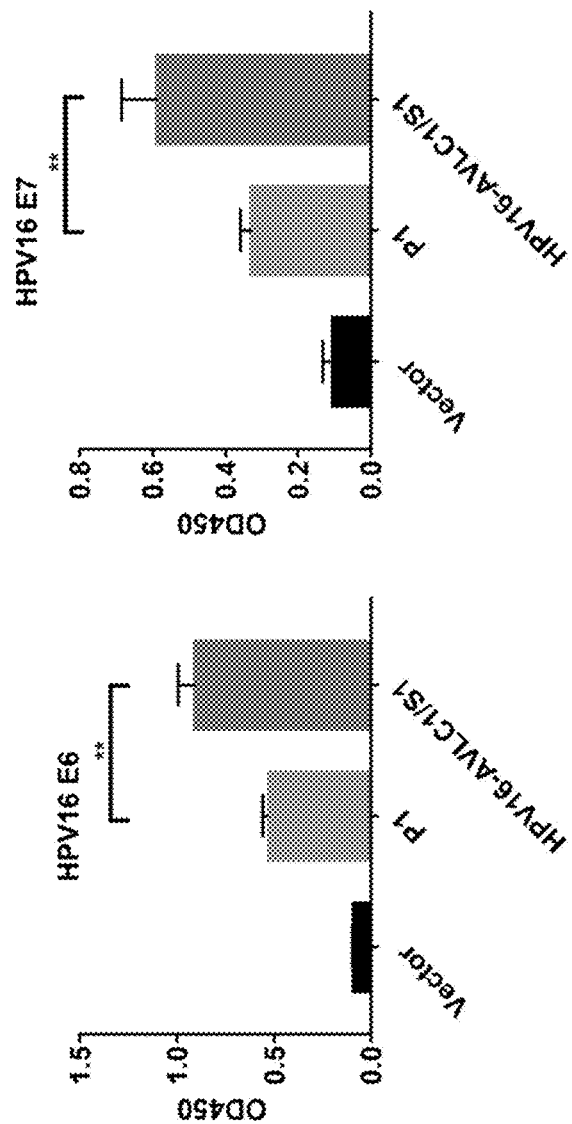
FIG. 6*a* shows the results of HPV16 E6 and E7 specific antibody detection.

The specific antibody test results of the HPV16 DNA vaccine were shown in FIG. 6a below. The results showed that the vaccine sequence of the invention can stimulate humoral immunity targeting E6 and E7 simultaneously, and is significantly higher than the humoral immunity response of control P1.

Figure 6B:
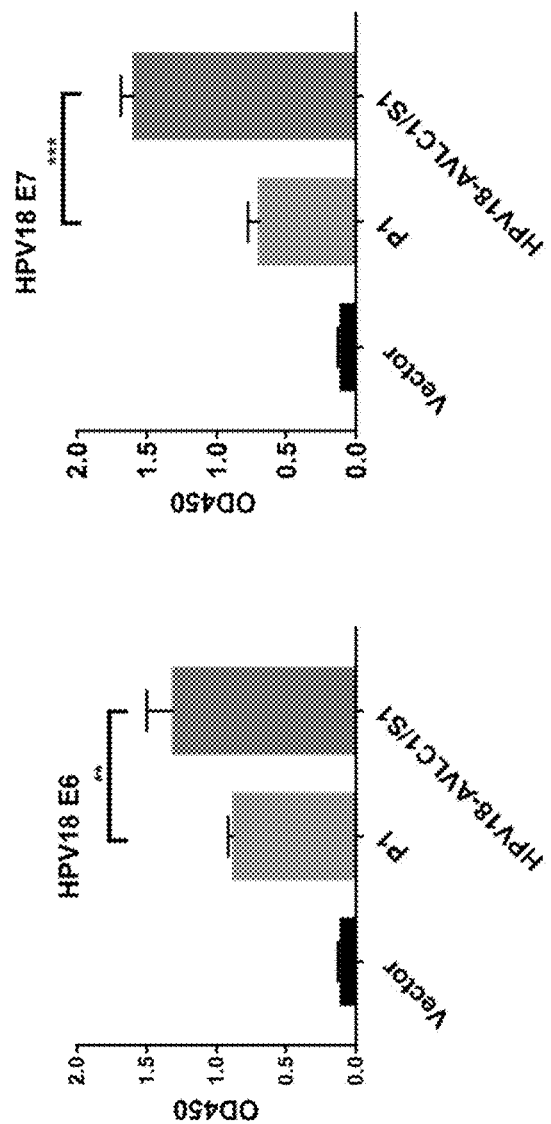
FIG. 6*b* shows the results of HPV18 E6 and E7 specific antibody detection.

The specific antibody test results of the HPV18 DNA vaccine were shown in FIG. 6b below. The results showed that the vaccine sequence of the invention can stimulate humoral immunity targeting E6 and E7 simultaneously, and is significantly higher than the humoral immunity response of control P2.

EXAMPLE 5: Treatment Effect on Tumors

The aim of this study is to determine whether therapeutic administration of HPV16-AVLS1/AVLC1 by standard subcutaneous injection can induce inhibition of TC-1 tumor growth or TC-1 tumor regression.

5.1 TC-1 Cell Culture and Inoculation TC-1 cells were grown in a 75 cm 2 flat bottom tissue culture flask in RPM medium containing 20 mM HEPES buffer, 10% FCS (Hy- clone), and 50 11M 2-Mercaptoethanol (Sigma), 1 mM sodium pyruvate (Gibco), 0.292 mg/mL glutamine, 100 U/mL penicillin/100 ug/mL Streptomycin/0.292 mg/mL glutamine, under sterile conditions. When the adherent TC-1 cells were approaching full growth, they were digested and collected using 0.25% trypsin/EDTA and reinoculated into more culture bottles to maintain logarithmic growth.

On the day of inoculation, TC-1 cells that grew exponentially were harvested using trypsin/EDTA. The cells were washed with the above RPMI medium, then washed twice with PBS, and then stained with Trypan blue and the living cells were counted with a blood cell counter. TC-1 cells were adjusted to $1 \times 10^6$ cells/mL in PBS to prepare for injection of 100 ul cell suspension/mouse (i.e. $1 \times 10^5$ cells).

All C57BL/6J mice were purchased from Vital River and raised under the condition in absence of specific pathogens. They were all female and aged 6-10 weeks at the beginning of the experiment.

TC-1 cells were injected subcutaneously into the back iliac bone of lightly anesthetized mice (inhalation of methoxyflurane), using BD 1 mL ultrafine insulin syringe (0.33 mm×12.7 mm). All mice were injected within two hours.

5.2 Vaccine Immunized Mice

After 3, 10, and 17 days of TC-1 vaccination, 30 μg HPV16-AVLS1/AVLC1 vaccine (dissolved in 40 μL TE) was subcutaneous delivered to both auricles by BD ultrafine insulin syringe, with 20 μL injections per auricle at a time. Empty vector AVL0318 and positive control P1 were injected with the same amount of plasmid in the same way, with 8 mice in each group. Tumor masses were examined and measured every day. The tumor volume was recorded, and when the tumor diameter of the mouse reaches 2000 mm³, it was ethically euthanized. Tumor size was observed daily.

5.3 Result Analysis

Figure 7:
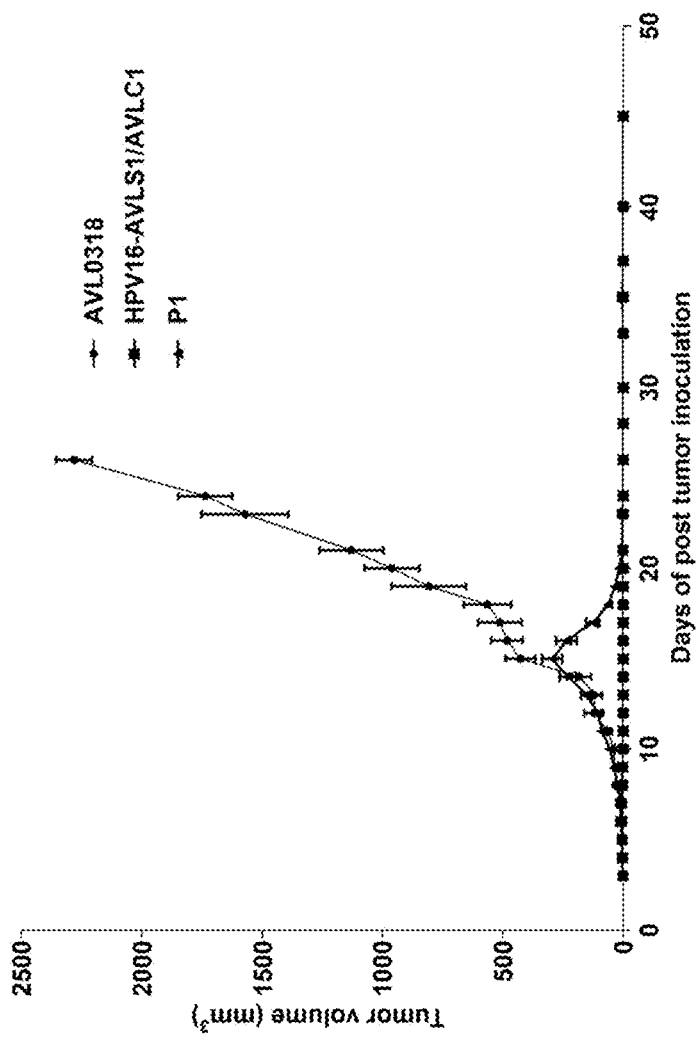
FIG. 7 shows the therapeutic effect of HPV16 vaccine on mouse TC-1 homograft tumor.

The results shown in FIG. 7 below revealed that both HPV16-AVLS1/AVLC1 and P1 can inhibit tumor growth inhibition, but HPV16-AVLS1/AVLC1 has a more significant inhibitory effect on tumor growth. No significant tumor growth was observed throughout the entire observation period, while P1 achieved a complete inhibitory effect on tumor growth basically after 20 days.

EXAMPLE 6: Effect of Tumor Prevention 6.1 TC-1 Cell Culture and Mouse Feeding were the same with Example 5 6.2 A total of 15 C57BL/6J female mice aged 6-10 weeks were divided into three groups, with five mice in each group. Each group was injected with the control plasmid AVL0318, vaccine sequence HPV16-AVLS1/AVLC1 and P1 three times, and 30 μg plasmids were injected into the auricles on days 0, 7, and 14, respectively. All mice were injected with $5 \times 10^5$ TC-1 tumor cells subcutaneously into the back iliac bone on the 21st day. On the day of inoculation, TC-1 cells were adjusted to $5 \times 10^6$ cells/mL in PBS, and each mouse was injected 100ul cell suspension. Then the growth of the tumor was detected every day.

6.3 Result Analysis

Figure 8:
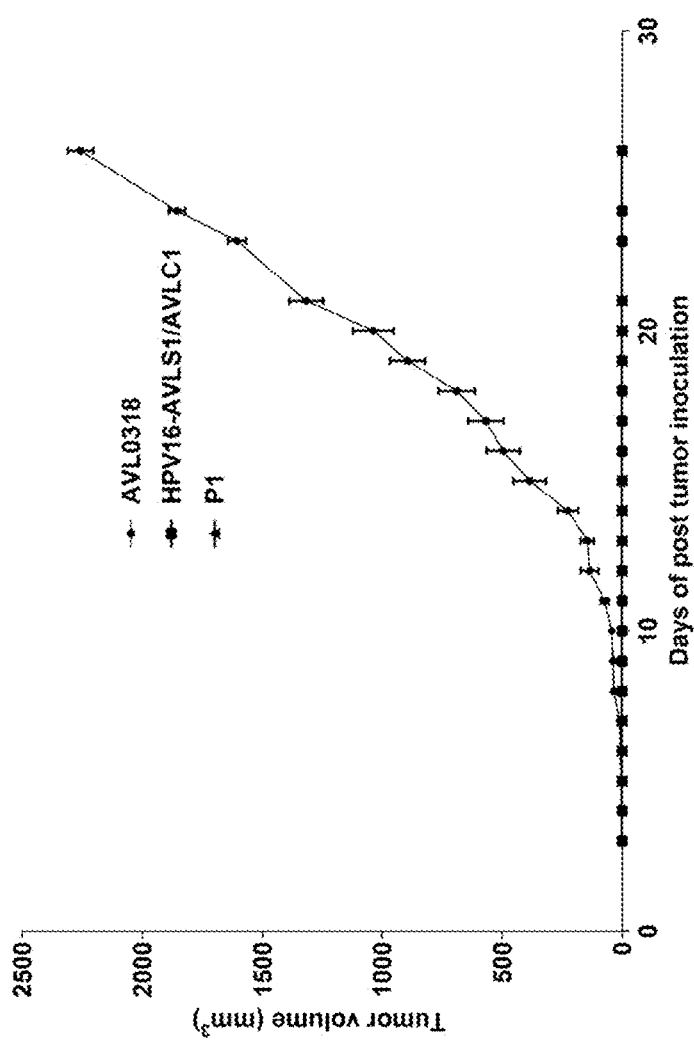
FIG. 8 shows the preventive effect of HPV16 vaccine on mouse TC-1 homograft tumor.

As shown in FIG. 8, compared to the control group, all mice in the HPV16-AVLS1/AVLC1 and P1 groups were unable to form tumors after inoculation with TC-1, indicating that HPV16-AVLS1/AVLC1 and P1 have a very significant effect of tumor prevention.

EXAMPLE 7: The *Escherichia coli* that can Express the SacB Gene Used in the Above Examples was Specifically Prepared as Follows 7.1 Design Primers

```
sacB-F1:
                                    (SEQ ID NO: 20)
ATCAATAATCAGACAACAAGATGAACATCAAAAAGTTTGC sacB-F2:
                                    (SEQ ID NO: 21)
TGATATAATGGTTTCGCCAAAAATCAATAATCAGACAACAAG sacB-F3:
                                    (SEQ ID NO: 22)
TAGACACACATCTTGTCATATGATATAATGGTTTCGCCAAAA sacB-R1:
                                    (SEQ ID NO: 23)
CTCAAGTTAGTATTTATTTGTTAACTGTTAATTGTCCTTG DH5-attB-down-F:
                                    (SEQ ID NO: 24)
TTAACAGTTAACAAATAAATACTAACTTGAGCGAAACGGGAAG DH5-attB-UP-R:
                                    (SEQ ID NO: 25)
GACAAGATGTGTGTCTACCAAAAAAGCAGGCTTCAACGGATTCA DH5 attB-up-F:
                                    (SEQ ID NO: 26)
GAAAGCCCAATCTTCACATCAATC DH5 attB-down-R:
                                    (SEQ ID NO: 27)
GCATCTGGCGTGGGATGATGTTCCT SgRNA:
                                    (SEQ ID NO: 28)
TCAAGTTAGTATAAAAAAGC
```

7.2. Obtaining p5/6 6/6-sacB Fragments

Use H73 vector as a template, and follow the procedure below as shown in table 1:

TABLE 1

| 2× superpfu PCR mix | 25 μl |
| sacB-F1 (10 μM) | 2 μl |
| sacB-R1 (10 μM) | 2 μl |
| H73 plasmid | 0.5 μl |
| ddH₂O | 20.5 μl |
| | |
| Total | 50 μl |

Amplification conditions:
94° C. 5 min
30Cycle (94° C. 30 sec, 55° C. 30 sec, 68° C. 30 sec)
10° C. Insulation The product after amplification was used as a template and the primes were replaced with sacB-F2/sacB-R1 primers, and according to the above procedure, a second amplification was performed.

The third amplification was carried out using amplification primers sacB-F3/sacB-R1, and the P5/6 6/6-sacB fragment was obtained after amplification.

7.3. AttB Homologous Arm Amplification

1) PCR amplification was performed using attB-UP-F/DH5-attB-UP-R, DH5-attB-down-F/DH5 attB-down-R primers according to the following system as shown in table 2:

TABLE 2

| 2× pfu PCR mix | 25 μl |
| primerF (10 μM) | 2 μl |
| Primer R (10 μM) | 2 μl |
| DH5α genomes DNA | 1 μl |
| ddH₂O | 20 μl |
| | |
| Total | 50 μl |

Amplification conditions
94° C. 5 min
32Cycle (94° C. 30 sec, 55° C. 30 sec, 68° C. 30 sec)
10° C. Insulation The results were shown in FIG. 9; wherein, M referred to the DL2000 DNA marker, up referred to upstream homologous segment of the amplified attB, SacB referred to the sacB-F3/R1 amplification product (P5/6 6/6-sacB), and down referred to downstream homologous arm segment of the amplified attB.

Figure 9:
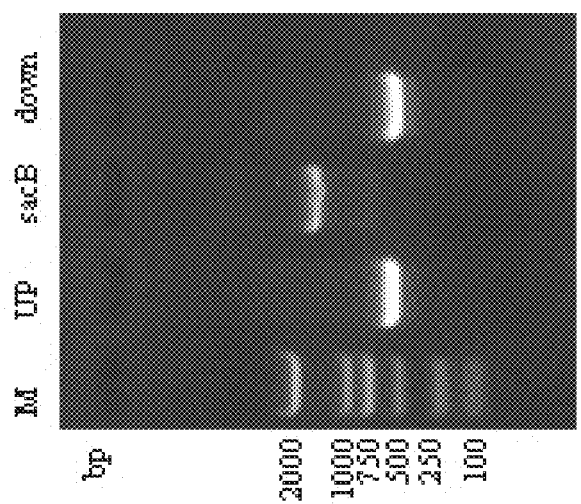
FIG. 9 shows the upstream and downstream homologous arms of attB and the SacB F3/R1 amplification electrophoresis detection map.
Figure 10:
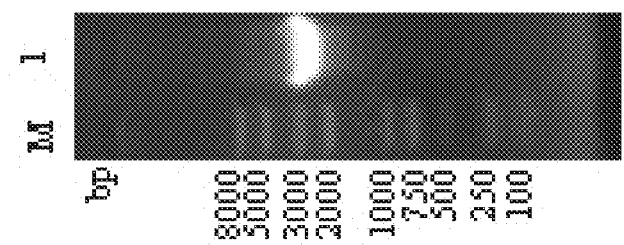
FIG. 10 shows the results of SacB-CRISPR fusion amplification.

2) Overlapping extension PCR amplification of the repaired homologous arms to obtain SacB-CRISPR nucleic acid fragments The three fragments, upstream homologous fragment of attB, sacBF3/R1 amplification product (P5/6/6-sacB), and downstream homologous arm fragment of attB from FIG. 9 were recycled by a PCR product purification kit for backup.

The overlapping PCR amplification was performed according to the following system as shown in table 3:

TABLE 3

| 2× superpfu PCR mix | 25 μl |
| DH5 attB-up-F (10 μM) | 2 μl |
| DH5 attB-down-R (10 μM) | 2 μl |
| UP fragment | 5 μl |
| P5/6 6/6-sacB fragment | 4 μl |
| down fragment | 5 μl |
| ddH₂O | 12 μl |
| | |
| Total | 50 μl |

Amplification condition
94° C. 5 min
2 Cycle (94° C. 30 sec, 50° C. 30 sec, 68° C. 1 min)
30Cycle (94° C. 30 sec, 55° C. 30 sec, 68° C. 1 min)
10° C. Insulation Agarose gel electrophoresis detection were carried out and the results were as shown in Figure wherein, M referred to the trans2K plus II DNAmarker, and 1 referred to the SacB-CRISPR nucleic acid fragment.

7.4 CRISPR Editing and Filtering AVL-DH5a (SacB)

7.4.1 Preparation of DH5a Electroporation Competent State

1) Activation culture by strain plate streaking was performed

2) The second day, monoclonal antibody was inoculated to 5 ml LB liquid medium for overnight cultivation at 37° C.

3) The next day, 1% was transferred to 50 ml LB liquid medium for growth to OD600 nm of about and the thallus was collected by centrifugation 4) 10% glycerol was used to wash for 3 times 5) Finally, 2 ml of 10% glycerol was used to resuspend the thallus, i.e. the prepared electroporation competent cells pTcCas9 (Tc resistance modified in our laboratory) plasmid was electrotransformed. 90 μL competent cells were added with 10 μL plasmids, placed on ice for 5 min, and electrotransformed in 2500Kv. 1 ml LB medium was added, and cultured at 30° C. for 1 h. Tc resistant plate was coated and cultured at 30° C. overnight.

7.4.2 Preparation of Cas9 DH5a Competent Cell

The Preparation Method is the Same as Above 7.4.3. Electrotransformation of SacB-CRISPR Nucleic Acid Fragments and sgRNA 7.4.4 Identification of SacB Insertion 10 monoclonal clones were selected for colony PCR identification, with the following primers:

```
DH5 attB-up-F:
                                        (SEQ ID NO: 29)
GAAAGCCCAATCTTCACATCAATC DH5 attB-down-R:
                                        (SEQ ID NO: 30)
AGGAACATCATCCCACGCCAGATGC
```

Figure 11:
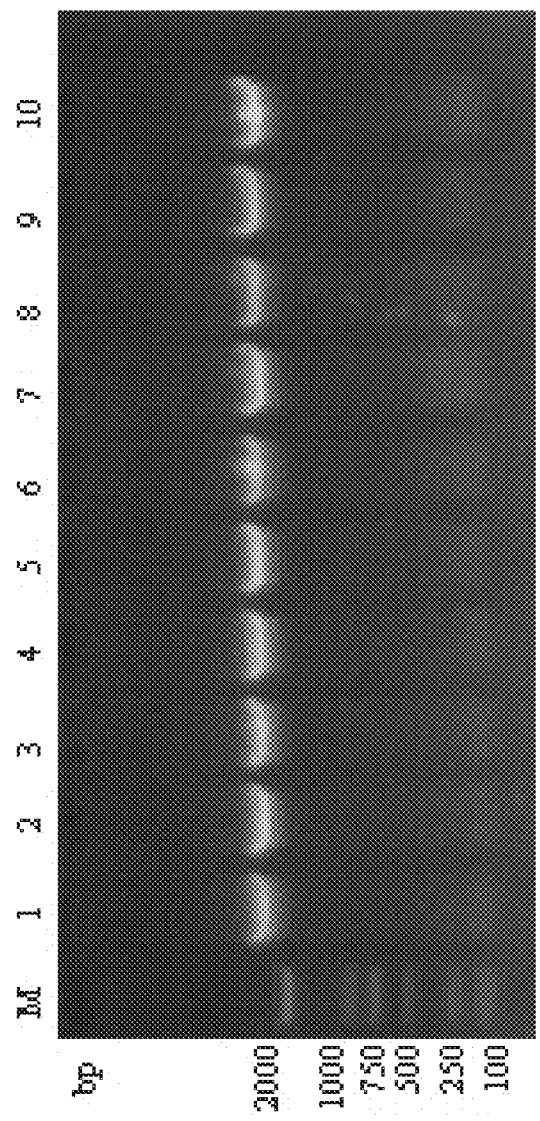
FIG. 11 shows AVL-DH5a (SacB) Colony PCR identification map.

As shown in FIG. 11, all 10 monoclonal clones were positive, where M referred to DL2000 DNA marker 1-10 was 10 clone numbers on the plate by a random selection The product in the figure was sent for sequencing, with sequencing primers

```
attb-JD-F:
                                        (SEQ ID NO: 31)
AATGCCAGCGCCAGACGGGAAAC attB-JD-R:
                                        (SEQ ID NO: 32)
CTCTGGCAAGCGCCTCGATTACT
```

Sequencing showed that SacB gene sequences had been inserted into all the monoclonal clones, and had been inserted into the target location correctly.

7.5. Resistance Elimination of Editing Bacterial [AVL-DH5α(SacB)]

The successfully edited bacteria were inoculated in non-resistant LB at 37° C., cultured overnight, and on the second day, they were diluted and applied onto LB non-resistant medium plate, and cultivated at 37° C.;

The monoclonal clones that grew out the second day were dot plated on LB (non-resistant) and LB (TC), LB (Cm) plates, and bacteria that did not grow on the two types of resistance were resistance-eliminating bacterial, and named as [AVL-DH5a (SacB)].

EXAMPLE 8 Exploration on Sucrose Sensitivity and Yield of the Amplified Plasmid of AVL-DH5α(SacB)

A sucrose sensitivity comparison was conducted for the provided *Escherichia coli* strain AVL-DH5α(SacB), and the *Escherichia coli* SacB expression strain DH5α att λ:: P5/6 6/6-RNA IN SacB, catR invented by Luke et al. using homologous recombination. The results showed that the strain provided by the present invention had higher sucrose sensitivity and passage stability. Specifically, refer to table 4.

TABLE 4

| | Strains | | | | | | |
|---|---|---|---|---|---|---|---|
| | AVL-DH5α(SacB) | | | DH5α attλ::P5/6 6/6-RNA-IN- SacB, catR | | | |
| Days | OD | Number of bacteria (CFU/10 μL) | Number of bacterial colony (6% Sucrose) | OD | Number of bacteria (CFU/10 μL) | Number of bacterial colony(6% Sucrose) | Number of bacterial colony in equal quantity |
| 1 | 1.321 | $1.06 \times 10^7$ | 35 | 1.364 | $1.09 \times 10^7$ | 207 | 201 |
| 2 | 1.309 | $1.05 \times 10^7$ | 51 | 1.299 | $1.04 \times 10^7$ | 279 | 282 |
| 3 | 1.528 | $1.22 \times 10^7$ | 50 | 1.328 | $1.06 \times 10^7$ | 298 | 343 |
| 4 | 1.614 | $1.29 \times 10^7$ | 60 | 1.402 | $1.12 \times 10^7$ | 331 | 381 |
| 5 | 1.582 | $1.27 \times 10^7$ | 62 | 1.4 | $1.12 \times 10^7$ | 386 | 438 |

Further comparison was made between the commonly used expression vector pcDNA3.1 and the AVL0318 vector of the present invention under the conditions of ampicillin antibiotics and sucrose, respectively. The results were as shown in table 5.

TABLE 5

| Plasmids | Volume of medium | Concentration (ng/μL) | Volume of elution (μL) | Yield (μg) | Relative yield |
|---|---|---|---|---|---|
| pcDNA3.1 | 15 mL LB (ampicillin) | 297.4 | 200 | 59.48 | 100% |
| AVL3018 | 15 mL LB (6% sucrose) | 362.9 | 200 | 72.58 | 122% |

The results revealed that although AVL0318 was amplified with AVL-DH5α(SacB) under antibiotic-free conditions, the yield of AVL0318 plasmid was still about 22% higher than that of pcDNA3.1, reflecting the superiority of the strain and expression vector of the present invention.

Although the present invention has been described in detail with general explanations, specific implementation methods, and experiments in the previous text, it is evident to those skilled in the art that some modifications or improvements can be made based on the present invention. Therefore, these modifications or improvements made on the basis of not deviating from the spirit of the present invention belong to the scope of protection claimed by the present invention.

The invention claimed is:

1. A nucleic acid sequence for the treatment and prevention of HPV infection diseases, comprising:
   sequence HPV16-AVLS1 and sequence HPV16-AVLC1 in a 1:1 ratio;
   and, sequence HPV18-AVLS1 and sequence HPV18-AVLC1 in a 1:1 ratio;
   wherein, the sequence AVLS1 and the sequence AVLC1 both include two concatenated protein E6 molecules, two L1 short peptides, two L2 short peptides, two concatenated protein E7 molecules, one PADRE sequence, and one adjuvant sequence; the N-terminal of sequence AVLS1 carries a mouse IgK secretion peptide sequence; the N-terminal of sequence AVLC1 carries a ubiquitin molecule;
   in the sequence HPV16-AVLS1 and sequence HPV16-AVLC1, the two L1 short peptides are of the sequences shown in SEQ ID No: 1, SEQ ID No: 2, respectively; the L2 short peptides are of the sequences shown in SEQ ID No: 5, SEQ ID No: 6, respectively;
   in the sequence HPV18-AVLS1 and sequence HPV18-AVLC1, the two L1 short peptides are of the sequences shown in SEQ ID No: 3, SEQ ID No: 4, respectively; the L2 short peptides are of the sequences shown in SEQ ID No: 7, SEQ ID No: 8, respectively;
   the PADRE sequence is the sequence shown in SEQ ID No: 9;
   the adjuvant sequence is the adjuvant peptide Beta-defensin-3, the sequence shown in SEQ ID No: 10;
   the mouse IgK secretion peptide sequence is the sequence shown in SEQ ID No: 11;
   the sequence of the ubiquitin molecule is the sequence shown in SEQ ID No: 12;
   the HPV16 fusion protein E6 sequence introduces C70G and I135T mutations, and the HPV18 fusion protein E6 sequence introduces C65G and I130T mutations;
   the HPV16 E7 protein sequence introduces C24G and E26G mutations, and the HPV18 E7 protein sequence introduces C27G and E29G mutations;
   the components are connected by AGA or AAY linkers;
   the adjuvant peptide is connected by a rigid linker EAAAK SEQ ID NO: 19.

2. The mRNA sequence converted from the nucleic acid sequence according to claim 1.

3. An HPV therapeutic nucleic acid vaccine, characterized in that: comprising the mRNA sequence according to claim 2.

4. The nucleic acid sequence according to claim 1, characterized in that: the nucleic acid sequence is the four sequences as shown in SEQ ID No: 13 to SEQ ID No: 16.

5. The mRNA sequence converted from the nucleic acid sequence according to claim 4.

6. An HPV therapeutic nucleic acid vaccine, characterized in that: comprising the mRNA sequence according to claim 5.

7. A recombinant vector, characterized in that: comprising an expression vector and the nucleic acid sequence according to claim 4.

8. An HPV therapeutic nucleic acid vaccine, characterized in that: comprising the recombinant vector according to claim 7.

9. An HPV therapeutic nucleic acid vaccine, characterized in that: comprising the nucleic acid sequences according to claim 4.

10. A recombinant vector, characterized in that: comprising an expression vector and the nucleic acid sequence according to claim 1.

11. An HPV therapeutic nucleic acid vaccine, characterized in that: comprising the recombinant vector according to claim 10.

12. The recombinant vector according to claim 10, the expression vector is an antibiotic-free AVL0318 vector.

13. An HPV therapeutic nucleic acid vaccine, characterized in that: comprising the recombinant vector according to claim 12.

14. A preparation method for amplifying the recombinant vector according to claim 12, characterized in that:
   comprising the following steps:
   1) Synthesizing four nucleic acid sequences of the vaccine sequences HPV16-AVLS1, HPV16-AVLC1, HPV18-AVLS1 and HPV18-AVLC1 by splicing the amino acid sequences of E6/E7 proteins, L1/L2 peptides, IgK, ubiquitin, PADRE, and adjuvant;
   2) Inserting the above four nucleic acid sequences into the vector PUC57 using HindIII and XhoI restriction enzyme sites, and then subcloning the vaccine sequences into the expression vector AVL0318; obtaining four recombinant vectors AVL0318-HPV16/18-AVLS1/AVLC1;
   3) Amplifying the plasmids of AVL0318-HPV16/18-AVLS1/AVLC1 using *Escherichia coli* AVL-DH5a;
   wherein, the genome sequence of *Escherichia coli* AVL-DH5a contains the SacB gene for constitutive expression and does not contain antibiotic selection markers; the sequence capable of expressing the SacB gene is shown as SEQ ID No: 17.

15. The preparation method according to claim 14, characterized in that: the preparation method of the *Escherichia coli* strain AVL-DH5a is as follows: the SacB gene is inserted into the attB site of the *Escherichia coli*.

16. The preparation method according to claim 15, characterized in that: the gene editing is achieved by a method comprising the following steps:
   i) PCR amplification of the upstream and downstream homologous arm gene sequences of the insertion site, p5/6 6/6-SacB gene sequence respectively, and overlapping extension PCR with the three sequences as templates to amplify the long fragment SacB-CRISPR nucleotide sequence; the nucleotide sequence of SacB-CRISPR is shown as SEQ ID No: 18;
   ii) Co-transforming the Cas9 expression plasmid, sgRNA, and the long fragment SacB-CRISPR nucleotide sequence into *Escherichia coli* DH5a competent cells, performing gene editing and homologous recombination repair, selecting single clones for culture, and verifying by PCR sequencing; finally, eliminating the resistance of tool plasmid and the edited strain by the temperature-sensitivity to obtain the AVL-DH5a strain suitable for target plasmid without antibiotics selection.

17. An HPV therapeutic nucleic acid vaccine, characterized in that: comprising the nucleic acid sequences according to claim 1.

* * * * *

```
                        SEQUENCE LISTING

Sequence total quantity: 32
SEQ ID NO: 1            moltype = AA  length = 45
FEATURE                 Location/Qualifiers
source                  1..45
                        mol_type = protein
                        organism = Synthetic construct
SEQUENCE: 1
GLUALATHRV ALTYRLEUPR OPROVALPRO VALSERLYSV ALVAL                    45

SEQ ID NO: 2            moltype = AA  length = 45
FEATURE                 Location/Qualifiers
source                  1..45
                        mol_type = protein
                        organism = Synthetic construct
SEQUENCE: 2
ASPTHRTYRA RGPHEVALTH RSERGLNALA ILEALACYSG LNLYS                    45

SEQ ID NO: 3            moltype = AA  length = 45
FEATURE                 Location/Qualifiers
source                  1..45
                        mol_type = protein
                        organism = Synthetic construct
SEQUENCE: 3
ASPASNTHRV ALTYRLEUPR OPROPROSER VALALAARGV ALVAL                    45

SEQ ID NO: 4            moltype = AA  length = 45
FEATURE                 Location/Qualifiers
source                  1..45
                        mol_type = protein
                        organism = Synthetic construct
SEQUENCE: 4
ASPTHRTYRA RGPHEVALGL NSERVALALA ILETHRCYSG LNLYS                    45

SEQ ID NO: 5            moltype = AA  length = 48
FEATURE                 Location/Qualifiers
source                  1..48
                        mol_type = protein
                        organism = Synthetic construct
SEQUENCE: 5
PROASPPHEL EUASPILEVA LALALEUHIS ARGPROALAL EUTHRSER                 48

SEQ ID NO: 6            moltype = AA  length = 48
FEATURE                 Location/Qualifiers
source                  1..48
                        mol_type = protein
                        organism = Synthetic construct
SEQUENCE: 6
PHEPHEGLYG LYLEUGLYIL EGLYTHRGLY SERGLYTHRG LYGLYARG                 48

SEQ ID NO: 7            moltype = AA  length = 48
FEATURE                 Location/Qualifiers
source                  1..48
                        mol_type = protein
                        organism = Synthetic construct
SEQUENCE: 7
ASPPROSERI LEVALTHRLE UILEGLUASP SERSERVALV ALTHRSER                 48
```

```
SEQ ID NO: 8              moltype = AA  length = 48
FEATURE                   Location/Qualifiers
source                    1..48
                          mol_type = protein
                          organism = Synthetic construct
SEQUENCE: 8
SERASPPHEM ETASPILEIL EARGLEUHIS ARGPROALAL EUTHRSER              48

SEQ ID NO: 9              moltype = AA  length = 39
FEATURE                   Location/Qualifiers
source                    1..39
                          mol_type = protein
                          organism = Synthetic construct
SEQUENCE: 9
ALALYSPHEV ALALAALATR PTHRLEULYS ALAALAALA                        39

SEQ ID NO: 10             moltype = AA  length = 135
FEATURE                   Location/Qualifiers
source                    1..135
                          mol_type = protein
                          organism = Synthetic construct
SEQUENCE: 10
GLYILEILEA SNTHRLEUGL NLYSTYRTYR CYSARGVALA RGGLYGLYAR GCYSALAVAL  60
LEUSERCYSL EUPROLYSGL UGLUGLNILE GLYLYSCYSS ERTHRARGGL YARGLYSCYS  120
CYSARGARGL YSLYS                                                  135

SEQ ID NO: 11             moltype = AA  length = 63
FEATURE                   Location/Qualifiers
source                    1..63
                          mol_type = protein
                          organism = Synthetic construct
SEQUENCE: 11
METGLUTHRA SPTHRLEULE ULEUTRPVAL LEULEULEUT RPVALPROGL YSERTHRGLY  60
ASP                                                               63

SEQ ID NO: 12             moltype = AA  length = 228
FEATURE                   Location/Qualifiers
source                    1..228
                          mol_type = protein
                          organism = Synthetic construct
SEQUENCE: 12
METGLNILEP HEVALLYSTH RLEUTHRGLY LYSTHRILET HRLEUGLUVA LGLUPROSER  60
ASPTHRILEG LUASNVALLY SALALYSILE GLNASPLYSG LUGLYILEPR OPROASPGLN  120
GLNARGLEUI LEPHEALAGL YLYSGLNLEU GLUASPGLYA RGTHRLEUSE RASPTYRASN  180
ILEGLNLYSG LUSERTHRLE UHISLEUVAL LEUARGLEUA RGGLYALA              228

SEQ ID NO: 13             moltype = DNA  length = 2088
FEATURE                   Location/Qualifiers
source                    1..2088
                          mol_type = other DNA
                          organism = Synthetic construct
SEQUENCE: 13
ggtaccgagc tcggatccgc cgccaccatg gaaacggaca cgctgctgct gtgggtcctg  60
ctgctgtggg tccccggatc gacgggagac ggatcgatgc accaaaaagcg aaccgctatg  120
tttcaggacc cccaggaacg accccgtaaa ctgccccagc tctgcacgga actgcaaacg  180
acgatccatg acatcatcct gaatgcgtg tactgcaagc aacagctcct gcgacgtgaa  240
gtctacgact ttgcttttcg cgacctgtgc atcgtctaca gagacggaaa ccctacgct  300
gtgggagaca aatgcctgaa gttttactcg aaaatctcgg aataccgcca ctactgctac  360
tcgctgtacg gaaccacgct cgaacagcaa tacaacagcc ccctatgcga cctgctaatc  420
cgctgcatca actgccaaaa gcctctctgc cctgaagaaa agcaacgcca tctcgacaaa  480
aagcaaagat tcacaacac gcgtggacga tggaccggac gatgcatgtc gtgctgcaga  540
tcgtcacgca cgcgtagaga aacccagctg gctgagcta tgcaccaaaa gcgaaccgct  600
atgtttcagg accccagga acgacccgt aaactgccc agctctgcac ggaactgcaa  660
acgacgatcc atgacatcat cctcgaatgc gtgtactgca gcaacagct cctgcgacgt  720
gaagtctacg acttttgcttt tcgcgacctg tgcatcgtct acagagacgg aaaccctac  780
gctgtgggag acaaatgcct gaagttttac tcgaaaatct cggaataccg ccactactgc  840
tactcgctgt acggaaccac gctcgaacag caatacaaca accccctatg cgacctgcta  900
atccgctgca tcaactgcca aaagcctctc tgccctgaag aaaagcaacg ccatctcgac  960
aaaaagcaaa gatttcacaa cacgcgtgga cgatggaccg gacgatgcat gtcgtgctgc  1020
agatcgtcac gcacgcgtag agaaacccag ctggctgctt acgaagctac cgtctacctc  1080
cccccgtgc cgtctcgaa agtggtcgct gcttacgaca cgtacagatt tgtgacctcg  1140
caagctatcg cttgccagaa ggctgctac cccgactttc tcgacatcgt cgctctgcat  1200
cgccccgctc tgacctcgcg agctgcttac ttttttggag gactgggaat cggaacggga  1260
tcggaacggg aggacgtgc tgcttacatg catggagata cgcctacgct ccatgaatat  1320
atgctcgatc tgcaacccga aacgaccgat tctctacggat atggacaact taacgactcg  1380
tcggaagaag aagatgaaat cgatggaccc gctggacaag ctgaaccgga ccgtgctcat  1440
tacaacatcg tcacgttttg ttgcaagtgt gactcgacgc tgcgactgtg cgtccaatcg  1500
acccacgtgg acatccgtac gctcgaagac ctgctcatgg aacgcttggg aatcgtctgc  1560
```

```
cccatctgct cgcagaaacc cgctggagct atgcatggag atacgcctac gctccatgaa  1620
tatatgctcg atctgcaacc cgaaacgacc gatctctacg gatatggaca acttaacgac  1680
tcgtcggaag aagaagatga aatcgatgga cccgctggac aagctgaacc cgaccgtgct  1740
cattacaaca tcgtcacgtt tgttgcaagt gtgactcgac gctgcgact gtgcgtccaa  1800
tcgacccacg tggacatccg tacgctcgaa gacctgctca tgggaacgct tggaatcgtc  1860
tgccccatct gctcgcagaa acccgctgga gctgctaaat tgtggctgc ttggacgctg  1920
aaggctgctg ctgaagctgc tgctaaagga atcatcaaca cgctgcaaaa gtactactgc  1980
cgtgtccgcg gaggacgatg cgctgtgctc tcgtgcctgc ccaaagaaga acagatcgga  2040
aagtgctcga cgagaggacg taaatgctgc cgccgaaaga ataatga                2088

SEQ ID NO: 14          moltype = DNA  length = 2247
FEATURE                Location/Qualifiers
source                 1..2247
                       mol_type = other DNA
                       organism = Synthetic construct
SEQUENCE: 14
ggtaccgagc tcggatccgc cgccaccatg caaatctttg tgaagacgct gacgggaaag   60
accatcacgc tcgaagtgga accctcggac acgatcgaaa acgtgaaagc taagatccga  120
gacaaggaag gaatccccc cgaccagcag agactgatct ttgctggaaa gcagctcgaa  180
gacggacgca cgctgtcgga ctacaacatc cagaaagaat cgacgctcca cctggtcctg  240
agactccgcg gagctatgca ccaaaagcga accgctatgt tcaggacccc caggaacga   300
ccccgtaaac tgccccagct ctgcacggaa ctgcaaacga catccatga catcatcctc  360
gaatgcgtgt actgcaagca acagctcctg cgacgtgaag tctacgactt tgcttttcgc  420
gacctgtgca tcgtctacag agacggaaac ccctacgctg tgggagacaa atgcctgaag  480
tttttactcga aaatctcgga ataccgccac tactgctact cgctgtacgg aaccacgctc  540
gaacagcaat acaacaaacc cctatgcgac ctgtaatcc gctgcatcaa ctgccaaaag  600
cctctctgcc ctgaagaaaa gcaacgccat ctcgacaaaa agcaaagatt tcacaacacg  660
cgtggacgat ggaccggacg atgcatgtcg tgctgcagat cgtcacgcac gcgtagagaa  720
acccagctgg ctggagctat gcaccaaaag cgaaccgcta tgtttcagga cccccaggaa  780
cgacccccgta aactgcccca gctctgcacg gaactgcaaa cgatccatg acatcatc    840
ctcgaatgcg tgtactgcaa gcaacagctc ctgcgacgtg aagtctacga ctttgctttt  900
cgcgacctgt gcatcgtcta cagagacgga aaccccctacg ctgtgggaga caatgcctg  960
aagtttttact cgaaaatctc ggaataccgc cactactgct actcgctgta cggaaccacg  1020
ctcgaacagc aatacaacaa acccctatgc gacctgctaa tccgctgcat caactgccaa  1080
aagcctctct gccctgaaga aaagcaacgc catctcgaca aaaagcaaag atttcacaac  1140
acgcgtggac gatggaccgg acgatgcatg tcgtgctgca gatcgtcacg cacgcgtaga  1200
gaaacccagc tggctgctta cgaagctacc gtctacctcc ccccgtgcc cgtctcgaaa  1260
gtggtcgctg cttacgacac gtacagattt gtgacctcgc aagcctatcg ttgccagaag  1320
gctgcttacc ccgactttct cgacatcgtc gctctgcatc gccccgctct gacctcgcga  1380
gctgcttact tttttggagg actgggaatc ggaacgggat cgggaacggg aggacgtgct  1440
gcttacatgc atggagatac gcctacgctc catgaatata tgctcgatct gcaacccgaa  1500
acgaccgatc tctacggata tggacaactt aacgactcgt cggaagaaga agatgaaatc  1560
gatgacccg ctggacaagc tgaacccgac cgtgctcatt acaacatgc acgtttttgt  1620
tgcaagtgtg actcgacgct gcgactgtgc gtccaatcga cccacgtgga catccgtacg  1680
ctcgaagacc tgctcatggg aacgcttgga atcgtcgcc catctgctc gcagaaaccc  1740
gctggagcta tgcatggaga tacgcctacg ctccatgaat atatgctcga tctgcaaccc  1800
gaaacgaccg atctctacgg atatggacaa cttaacgact cgtcggaaga agaagatgaa  1860
atcgatggac ccgctggaca agctgaaccc gaccgtgctc attacaacat cgtcacgttt  1920
tgttgcaagt gtgactcgac gctgcgactg tgcgtccaat cgacccacgt ggacatccgt  1980
acgctcgaag acctgctcat gggaacgctt ggaatcgtct gccccatctg ctcgcagaaa  2040
cccgctggag ctgctaaatt gtggctgct tggacgctga aggctgctg ctgaagctgc    2100
tgctaaaggaa tcatcaacac gctgcaaaag tactactgcc gtgtccgcgg aggacgatgc  2160
gctgtgctct cgtgcctgcc caaagaagaa cagatcggaa agtgctcgac gagaggacgt  2220
aaatgctgcc gccgaaagaa ataatga                                      2247

SEQ ID NO: 15          moltype = DNA  length = 2139
FEATURE                Location/Qualifiers
source                 1..2139
                       mol_type = other DNA
                       organism = Synthetic construct
SEQUENCE: 15
ggtaccgagc tcggatccgc cgccaccatg gaaacggaca cgctgctgct gtgggtcctg   60
ctgctgtggg tccccggatc gacgggagac ggatcgatgg ctcgctttga agacccaacg  120
cgccgaccct acaagctccc cgacctgtgc acggaactga cgtcgcaagac atc         180
gaaatcacct cgtgtactg caagacggtc ctgaactca cggaagtgtt tgaatttgct    240
tttaaagacc tctttgtggt ctacagagac tcgatcccgc atgctgctgg acataaatgc  300
atcgactttt actcgcgcat cagagaactc agacattact ctgactcggt ctacggagac  360
acgctggaaa agctgacgaa cacgggactc tacaacctcc tgatccgttg cctgcgttgc  420
cagaaaccgc tcaacccagc tgaaaagctg cgccacctca acgaaaaacg acgttttcac  480
aacacggctg acactacag aggacagtgc cattcgtgct gcaaccgagc tcgtcaggaa  540
cgactccaac gacgcagaga aacgcaagtg ctggagctga tggctcgctt tgaagaccca  600
acgcgccgac cctacaagct ccccgacctg tgcacggaac tgaacacgtc gctgcaagac  660
atcgaaatca cctgcgtgta ctgcaagacg gtcctgaac tcacggaagt gtttgaattt  720
gcttttaaag acctctttgt ggtctacaga gactcgatcc cgcatgctaa               780
tgcatcgact tttactcgcg catcagagaa ctcagacatt actctgactc ggtctacgga  840
gacacgctgg aaaagctgac gaacacggga ctctacaacc tcctgatccg ttgcctgcgt  900
tgccagaaac cgctcaaccc agctgaaaag ctgcgccacc tcaacgaaaa acgacgtttt  960
cacaacacg ctggacacta cagaggacag tgccattcgt gctgcaaccg agctcgtcag  1020
gaacgactcc aacgacgcag agaaacgcaa gtggctgctt acgacaacac ggtgtacctc  1080
```

```
cccccccct cggtcgctag agtggtcgct gcttacgaca cgtaccgttt tgtgcaatcg   1140
gtcgctatca cctgccagaa agctgcttac gaccctcga  tcgtgacgct gatcgaagac   1200
tcgtcggtgg tcacgtcggg agctcccgct gcttactcgg actttatgga catcatccgc   1260
ctccaccgac ccgctctgac gtcgagagct gcttacatgc atggacccaa agctacgctg   1320
caagacatcg tgctccatct cgaacccaa  aacgaaatcc cggtcgacct cctcggacac   1380
ggacaactct cggactcgga agaagaaaac gacgaaatcg acggagtgaa ccatcaacac   1440
ctcccagctc gacgcgctga accacaacgt cacacgatcg tgtgcatgtg ctgcaagtgc   1500
gaagctagaa tcgaactggt cgtggaatcg tctgctgacg acctgcgagc ttttcagcag   1560
ctgtttctga acaccctgtc gtttgtctgc ccgtggtgcg cttcgcagca ggctggagct   1620
atgcatggac ccaaagctac gctgcaagac atcgtgctcc atctcgaacc ccaaaacgaa   1680
atcccggtcg acctcctcgg acacggacaa ctctcggact cggaagaaga aaacgacgaa   1740
atcgacgagt gaaccatcaa cacctcccag ctcgacgcg  ctgaaccaca cgtcacacg    1800
atgctgtgca tgtgctgcaa gtgcgaagct agaatcgaac tggtcgtgga atcgtctgct   1860
gacgacctgc gagcttttca gcagctgttt ctgaacaccc tgtcgtttgt ctgcccgtg    1920
tgcgcttcgc agcaggctgg agctgctaaa tttgtggctg cttggacgct gaaggctgct   1980
gctgaagctg ctgctaaagg aatcatcaac acgctgcaaa agtactactg ccgtgtccgc   2040
ggaggacgat gcgctgtgct ctcgtgcctg cccaaagaag aacagatcgg aaagtgctcg   2100
acgagaggac gtaaatgctg ccgccgaaag aaataatga                          2139

SEQ ID NO: 16         moltype = DNA  length = 2298
FEATURE               Location/Qualifiers
source                1..2298
                      mol_type = other DNA
                      organism = Synthetic construct
SEQUENCE: 16
ggtaccgagc tcggatccgc cgccaccatg caaatctttg tgaagacgct gacgggaaag   60
accatcacgc tcgaagtgga accctcggac acgatcgaaa acgtgaaagc taagatccag   120
gacaaggaag gaatccccc  cgaccagcag agactgatct tgctggaaa  gcagctcgaa   180
gacggacgca cgctgtcgga ctacaacatc cagaaagaat cgacgctcca cctggtcctg   240
agactccgcg gagctatgc  tcgctttgaa gacccaacgc gccgaccta  caagctcccc   300
gacctgtgca cggaactgaa cacgtcgctg caagacatcg aaatcacctg cgtgtactgc   360
aagacggtcc tggaactcac ggaagtgttt gaatttgctt ttaaagacct ctttgtggtc   420
tacagagact cgatcccgca tgctgctgga cataaatgca tcgactttta ctcgcgcatc   480
agagaactca gacattactc tgactcggtc tacggagaca cgctggaaaa gctgaccgac   540
acgggactct acaacctcct gatccgttgc ctgcgttgcc agaaaccgct caacccagct   600
gaaaagctgc gccacctcaa cgaaaaacga cgttttcaca acacggctgg acactacaga   660
ggacagtgcc attcgtgctg caaccgagct cgtcaggaac gactccaacg acgcagaaga   720
acgcaagtgg ctggagctat ggctcgcttt gaagacccaa cgcgccgacc ctacaagctc   780
cccgacctgt gcacggaact gaacacgtcg ctgcaagaca tcgaaatcac ctgcgtgtac   840
tgcaagacgg tcctggaact cacggaagtg tttgaatttg cttttaaaga cctctttgtg   900
gtctacagag actcgatccc gcatgctgct ggacataaat gcatcgactt ttactcgcgc   960
atcagagaac tcagacatta ctctgactcg gtctacggag acacgctgga aaagctgacg   1020
aacacggaac tctacaacct cctgatccgt tgcctgcgtt gccagaaacc gctcaaccca   1080
gctgaaaagc tgcgccacct caacgaaaaa cgacgttttc acaacacggc tggacactac   1140
agaggacagt gccattcgtg ctgcaaccga gctcgtcagg aacgactcca acgacgcaga   1200
gaaacgcaag tggctgctta cgacaacacg gtgtacctcc cccccccctc ggtcgctaga   1260
gtggtcgctg cttacgacac gtaccgtttt gtgcaatcgg tgctatcac  ctgccagaaa   1320
gctgcttacg accctcgat  cgtgacgctg atcgaagact cgtcggtggt cacgtcggga   1380
gctcccgctg cttactcgga ctttatggac atcatccgcc tccaccgacc cgctctgacg   1440
tcgagagctg cttacatgca tggacccaaa gctacgctgc aagacatcgt gctccatctc   1500
gaacccaaa  acgaaatccc ggtcgacctc ctcggacacg gacaactctc ggactcggaa   1560
gaagaaaacg acgaaatcga cggagtgaac catcaacacc tcccagctcg acgcgctgaa   1620
ccacaacgtc acgatgct   gtgcatgtgc tgcaagtgcg aagctagaat cgaactggtc   1680
gtggaatcgt ctgctgacga cctgcgagct tttcagcagc tgtttctgaa caccctgtcg   1740
tttgtctgcc cgtggtgcgc ttcgcagcag gctggagcta tgcatgacc  caaagctacg   1800
ctgcaagaca tcgtgctcca tctcgaaccc aaaacgaaa  tcccggtcga cctcctcgga   1860
cacggacaac tctcggactc ggaagaagaa aacgacgaaa tcgacggagt gaaccatcaa   1920
cacctcccag ctcgacgcgc tgaaccacac cgtcacacga tgctgtgcat gtgctgcaag   1980
tgcgaagcta gaatcgaact ggtcgtggaa tcgtctgctg acgacctgcg agcttttcag   2040
cagctgtttc tgaacaccct gtcgtttgtc tgcccgtggt gcgcttcgca gcaggctgg    2100
gctgctaaat ttgtggctgc ttggacgctg aaggctgctg ctgaagctgc tgctaaagga   2160
atcatcaaca cgctgcaaaa gtactactgc cgtgtccgcg gaggacgatg cgctgtgctc   2220
tcgtgcctgc ccaaagaaga acagatcgga aagtgctcga cgagaggacg taaatgctgc   2280
cgccgaaaga aataatga                                                 2298

SEQ ID NO: 17         moltype = DNA  length = 1422
FEATURE               Location/Qualifiers
source                1..1422
                      mol_type = other DNA
                      organism = Synthetic construct
SEQUENCE: 17
atgaacatta aaaaattcgc gaaacaggcg accgttctga ccttcaccac cgcgctgctg   60
gcgggcggtg cgacccaggc gttcgctaaa gaaaccaacc agaaaccgta taagaaaacc   120
tacggtattt ctcacattac ccgccacgat atgctgcaga tcccggaaca gcagaaaaac   180
gaaaaatacc aggttccgga attcgacagc tccaccatca aaaacatcag cagcgcgaaa   240
ggcctggatg tttgggattc ttggccgctg cagaacgctg atggcaccgt cgcgaactac   300
cacggctatc atattgtgtt cgcgctggcg gcgacccga  aaacgcggat gacacctct    360
atctacatgt tctaccagaa agttggtgaa accagtatcg acagctggaa aaacgcaggc   420
cgtgttttca aagatagcga taaattcgat gcgaacgata gcatcctgaa agatcagact   480
```

```
caggaatgga gcggtagcgc taccttcacc tccgacggca aaattcgtct gttctacacc    540
gatttcagcg gcaaacacta tggtaaacag accctgacca ccgcgcaggt gaacgtgtcc    600
gcgtccgact cctctctgaa catcaacggc gttgaagatt acaaatctat cttcgatggt    660
gacggcaaaa cttatcagaa cgttcagcag ttcatcgatg aaggcaacta ctcttctggc    720
gataaccaca ccctgcgtga tccgcactac gttgaagata aaggccacaa atacctggtt    780
ttcgaagcta acaccggcac cgaagatggc taccagggtg aagaaagcct gttcaacaaa    840
gcgtattacg gtaaatctac cagctttttc cgtcaggaat cccagaaact gctgcagagc    900
gataaaaaac gtaccgcgga actggcgaac ggcgcgctgg gcatgatcga actgaacgat    960
gattacaccc tgaaaaagt tatgaaaccg ctgatcgta gcaacaccgt taccgatgaa   1020
atcgaacgtg cgaacgtttt caaaatgaac ggcaaatggt acctgttcac cgactctcgt   1080
ggtagcaaaa tgaccatcga tggtatcacc tctaacgaca tctacatgct gggttacgtt   1140
agcaacagcc tgaccggtcc gtacaaaccg ctgaacaaaa ccggtctggt tctgaaaatg   1200
gacctggatc cgaacgacgt taccttcacc tatagccatt tcgcggtgcc gcaggcgaaa   1260
ggtaacaacg tggtgatcac ctcctacatg accaaccgtg gtttctacgc tgataaacag   1320
agcaccttcg cgccgagctt cctgctgaac atcaaaggta agaaaaccag cgtcgttaaa   1380
gacagcatcc tggaacaggg ccagctgacc gttaacaaat aa                      1422

SEQ ID NO: 18           moltype = DNA   length = 2474
FEATURE                 Location/Qualifiers
source                  1..2474
                        mol_type = other DNA
                        organism = Synthetic construct
SEQUENCE: 18
gaaagcccaa tcttcacatc aatcggtttt tcacctgtac cgtacagagt aattccaccc     60
ggagcggcag ggacatatac cgttccctga tactcaccag gcatcacggc aatatactgg    120
cgcttgttgg tacgcttgat aattgccgca tctaccgccg tctgaatcgt ggtatgcgtt    180
acaccttgag tgcccgccgg gccgacaaca aagtcaggtt gcgcaggcag ggtaatcggg    240
gaaggattcc acgctgcagc acctggtgtc agggatgcaa aatagtgttg agcatcgaaa    300
ttctgcgctt ctttttgccga cagaatcggg cgagaagagg taccaggcgc ggtttgatca    360
gaaggacgtt gatcgggcgg ggttgagcta caggcggtca gcgtcacgcc aaaagccaat    420
gccagcgcca gacgggaaac tgaaaatgtg ttcacaggtt gctccgggct atgaaataga    480
aaaatgaatc cgttgaagcc tgcttttttg gtagacacac atcttgtcat atgatataat    540
ggtttcgcca aaaatcaata atcagacaac aagatgaaca ttaaaaaatt cgcgaaacag    600
gcgaccgttc tgaccttcac caccgcgctg ctggcggggc gtgcgaccca ggcgttgccc    660
aaagaaacca accgaaacc gtataaagaa acctacggta tttctcacat taccgccac    720
gatatgctgc agatcccgga acagcagaaa acgaaaaat accaggttcc ggaattcgac    780
agctccacca tcaaaaacat cagcagccgcg aaaggcctgg atgtttggga ttcttggccg    840
ctgcagaacg ctgatggcac cgtcgcgaac taccacggct atcatattgt gttcgcgctg    900
gcgggcgacc cgaaaaacgg ggatgacacc tctatctaca tgttctacca gaaagttggt    960
gaaaccagta tcgacagctg gaaaaacgca ggccgtgttt tcaaagatag cgataaattc   1020
gatgcgaacg atagcatcct gaaagatcag actcaggaat ggagcggtag cgctaccttc   1080
acctccgacg gcaaaattcg tctgttctac accgatttca gcggcaaaca ctatggtaaa   1140
cagaaccgtga ccaccgcgca ggtgaacgtg tccgcgtccg actcctctct gaacatcaac   1200
ggcgttgaag attacaaatc tatcttcgat ggtgacggca aaacttatca gaacgttcag   1260
cagttcatcg atgaaggcaa ctactcttct ggcgataacc acaccctgcg tgatccgcac   1320
tacgttgaag ataaaggcca caaatacctg gttttcgaag ctaacaccgg caccgaagat   1380
ggctaccagg gtgaagaaag cctgttcaac aaagcgtatt acggtaaatc taccagcttt   1440
ttccgtcagg aatcccagaa actgctgcag agcgataaaa aacgtaccgc ggaactggcg   1500
aacggcgcgc tgggcatgat cgaactgaac gatgattaca ccctgaaaaa agttatgaaa   1560
ccgctgatcg ctagcaacac cgttaccgat gaaatcgaac gtgcgaacgt tttcaaaatg   1620
aacggcaaat ggtacctgtt caccgactct cgtggtagca aaatgaccat cgatggtatc   1680
acctctaacg acatctacat gctgggttac gttagcaaca gcctgaccgg tccgtacaaa   1740
ccgctgaaca aaaccggtct ggttctgaaa atggacctgg atccgaacga cgttaccttc   1800
acctatagcc atttcgcggt gccgcaggcg aaaggtaaca acgtggtgat cacctcctac   1860
atgaccaacc gtggtttcta cgctgataaa cagagcacct tcgcgccgag cttcctgctg   1920
aacatcaaag gtaagaaaac cagcgtcgtt aaagacagca tcctggaaca gggccagctg   1980
accgttaaca aataaatact aacttgagcg aaacgggaag gtaaaagac aaaaagttgt   2040
ttttaatacc tttaagtgat accagatggc attgcgccat ctggcagagt gattaactaa   2100
acatcgcagt aatcgaggcg cttgccagag agtggaaatg aacgttaaac ccgaccatcg   2160
cgccgctggc accttcatcg acatcaatac gttctatatc cagcgcgtga acggtaaaaa   2220
tgtagcgatg agtttcgcct ttcggcggtg ctgcgccatc gtaccggtt ttaccaaagt   2280
cggtacgcgt ctgcaaaacg ccgtctgca ttgctaccag accagagcca aacccttgcg   2340
gtaatacgcg ggtatcagcg ggtaagttaa caactaccca gtgccaccag ccggagccgg   2400
ttggcgcatc cgggtcgtag caggtgacaa caaaacttt cgttcccgca ggaacatcat   2460
cccacgccag atgc                                                     2474

SEQ ID NO: 19           moltype = AA    length = 15
FEATURE                 Location/Qualifiers
source                  1..15
                        mol_type = protein
                        organism = Synthetic construct
SEQUENCE: 19
GLUALAALAA LALYS                                                      15

SEQ ID NO: 20           moltype = DNA   length = 40
FEATURE                 Location/Qualifiers
source                  1..40
                        mol_type = other DNA
                        organism = Synthetic construct
```

```
SEQUENCE: 20
atcaataatc agacaacaag atgaacatca aaaagtttgc                              40

SEQ ID NO: 21           moltype = DNA   length = 42
FEATURE                 Location/Qualifiers
source                  1..42
                        mol_type = other DNA
                        organism = Synthetic construct
SEQUENCE: 21
tgatataatg gtttcgccaa aaatcaataa tcagacaaca ag                           42

SEQ ID NO: 22           moltype = DNA   length = 42
FEATURE                 Location/Qualifiers
source                  1..42
                        mol_type = other DNA
                        organism = Synthetic construct
SEQUENCE: 22
tagacacaca tcttgtcata tgatataatg gtttcgccaa aa                           42

SEQ ID NO: 23           moltype = DNA   length = 40
FEATURE                 Location/Qualifiers
source                  1..40
                        mol_type = other DNA
                        organism = Synthetic construct
SEQUENCE: 23
ctcaagttag tatttatttg ttaactgtta attgtccttg                              40

SEQ ID NO: 24           moltype = DNA   length = 43
FEATURE                 Location/Qualifiers
source                  1..43
                        mol_type = other DNA
                        organism = Synthetic construct
SEQUENCE: 24
ttaacagtta acaaataaat actaacttga gcgaaacggg aag                          43

SEQ ID NO: 25           moltype = DNA   length = 44
FEATURE                 Location/Qualifiers
source                  1..44
                        mol_type = other DNA
                        organism = Synthetic construct
SEQUENCE: 25
gacaagatgt gtgtctacca aaaaagcagg cttcaacgga ttca                         44

SEQ ID NO: 26           moltype = DNA   length = 24
FEATURE                 Location/Qualifiers
source                  1..24
                        mol_type = other DNA
                        organism = Synthetic construct
SEQUENCE: 26
gaaagcccaa tcttcacatc aatc                                               24

SEQ ID NO: 27           moltype = DNA   length = 25
FEATURE                 Location/Qualifiers
source                  1..25
                        mol_type = other DNA
                        organism = Synthetic construct
SEQUENCE: 27
gcatctggcg tgggatgatg ttcct                                              25

SEQ ID NO: 28           moltype = DNA   length = 20
FEATURE                 Location/Qualifiers
source                  1..20
                        mol_type = other DNA
                        organism = Synthetic construct
SEQUENCE: 28
tcaagttagt ataaaaaagc                                                    20

SEQ ID NO: 29           moltype = DNA   length = 24
FEATURE                 Location/Qualifiers
source                  1..24
                        mol_type = other DNA
                        organism = Synthetic construct
SEQUENCE: 29
gaaagcccaa tcttcacatc aatc                                               24

SEQ ID NO: 30           moltype = DNA   length = 25
FEATURE                 Location/Qualifiers
source                  1..25
                        mol_type = other DNA
```

```
                        organism = Synthetic construct
SEQUENCE: 30
aggaacatca tcccacgcca gatgc                                              25

SEQ ID NO: 31           moltype = DNA  length = 23
FEATURE                 Location/Qualifiers
source                  1..23
                        mol_type = other DNA
                        organism = Synthetic construct
SEQUENCE: 31
aatgccagcg ccagacggga aac                                                23

SEQ ID NO: 32           moltype = DNA  length = 23
FEATURE                 Location/Qualifiers
source                  1..23
                        mol_type = other DNA
                        organism = Synthetic construct
SEQUENCE: 32
ctctggcaag cgcctcgatt act                                                23
```